United States Patent
Dawson

(10) Patent No.: US 7,195,877 B2
(45) Date of Patent: Mar. 27, 2007

(54) CYTOCHROME P450 GENETIC VARIATIONS

(75) Inventor: Elliott P. Dawson, Murfreesboro, TN (US)

(73) Assignee: Bioventures, Inc., Murfreesboro, TN (US)

( * ) Notice: Subject to any disclaimer, the term of this patent is extended or adjusted under 35 U.S.C. 154(b) by 433 days.

(21) Appl. No.: 10/712,363

(22) Filed: Nov. 12, 2003

(65) Prior Publication Data

US 2004/0072235 A1   Apr. 15, 2004

Related U.S. Application Data

(63) Continuation of application No. PCT/US03/21468, filed on Jul. 9, 2003, and a continuation-in-part of application No. 10/360,790, filed on Jul. 18, 2002, now abandoned.

(60) Provisional application No. 60/306,675, filed on Jul. 20, 2001.

(51) Int. Cl.
  *C12Q 1/68*   (2006.01)
  *C12P 19/34*  (2006.01)
  *C07H 21/04*  (2006.01)

(52) U.S. Cl. ................... 435/6; 435/91.2; 536/23.2; 536/24.33

(58) Field of Classification Search ............. None
  See application file for complete search history.

(56) References Cited

U.S. PATENT DOCUMENTS 6,309,823 B1 * 10/2001 Cronin et al. ............... 435/6

2003/0044797 A1 * 3/2003 Risinger et al. ............. 435/6
2003/0083485 A1 * 5/2003 Milos et al. ................ 536/23.2
2003/0170651 A1 * 9/2003 Guida et al. ................ 435/6

FOREIGN PATENT DOCUMENTS

WO   WO 02/38589 A2   5/2002

OTHER PUBLICATIONS

GenBank Accession No. M33388 (1994). 5 pages. Accessed Aug. 9, 2006.*
Buck et al. Design strategies and performance of custom DNA sequencing primers. Biotechniques (1999) 27: 528-536.*
Longo et al. Use of uracil DNA glycosylase to control carry-over contamination in polymerase chain reactions. Gene (1990) 93(1): 125-128.*

* cited by examiner

*Primary Examiner*—Jeffrey Fredman
*Assistant Examiner*—Angela Bertagna
(74) *Attorney, Agent, or Firm*—David A. Farah; Sheldon Mak Rose & Anderson PC

(57) ABSTRACT

A primer set used to screen a polynucleotide sample to detect and identify variants in the Cytochrome P450 isoenzyme 2D6 (CYP2D6) gene. A method of screening a polynucleotide sample to detect and identify the presence of one or more than one variant in the CYP2D6 gene in the sample. A method of predicting the potential for altered metabolism of a substance, including one or more than one pharmaceutical drug, by a first individual compared to a second control individual, where the substance is metabolized by the CYP2D6 isoenzyme, and where the second control individual is homozygous for the wild type allele of the CYP2D6*1, SEQ ID NO:1. A method of screening a population to detect and identify the presence of one or more than one variant in the CYP2D6 gene. A purified or isolated variant of SEQ ID NO:1. A purified or isolated variant of SEQ ID NO:3.

53 Claims, No Drawings

CYTOCHROME P450 GENETIC VARIATIONS

CROSS-REFERENCE TO RELATED APPLICATION

The present is a continuation of PCT Patent Application PCT/US03/21468 filed Jul. 9, 2003 and a continuation-in-part of U.S. patent application Ser. No. 10/360,790, filed Jul. 18, 2002, now abandoned which claims the benefit of U.S. Provisional Patent Application 60/306,675 filed Jul. 20, 2001, the contents of which are incorporated herein by reference in their entirety.

BACKGROUND

Adverse reactions to pharmaceutical drugs cause significant morbidity and mortality. Further, when the rate or severity of the adverse reactions causes the withdrawal of a pharmaceutical drug from the market, adverse reactions also cause considerable financial losses to pharmaceutical companies.

A large portion of endobiotics and xenobiotics, including many classes of pharmaceutical drugs, is metabolized by cytochrome p450 super family of enzymes present in human liver tissue. Cytochrome P450 2D6 (CYP2D6) is an isoenzyme of the cytochrome p450 super family and is responsible for the metabolism of many pharmaceutical drugs in commonly prescribed drug classes such as antiarrhythmics, β-receptor blockers, neuroleptics, selective serotonin reuptake inhibitors and antidepressants. Examples of pharmaceutical drugs metabolized by CYP2D6 include amitriptyline, codeine, desipramine, haloperidol, metopropol, tamoxifen and timolol.

There is considerable genetic polymorphism in CYP2D6. Polymorphic variants of CYP2D6 can result in altered metabolism of pharmaceutical drugs due to impaired CYP2D6 function. The altered metabolism can be increased metabolism, decreased metabolism or a shift in the metabolic ratio of enantiomeric forms of a pharmaceutical drug in a mixture of enantiomers. The rate of altered pharmaceutical drugs metabolism due to polymorphic variants of CYP2D6 has been estimated at 7% of Caucasian Americans, 2% of African American and 1% of Asian Americans. However, the true rate of altered pharmaceutical drugs metabolism due to polymorphic variants of CYP2D6 and the distribution of CYP2D6 variants remains poorly understood, especially in individuals of non-northern European descent. Further, there remains large numbers of CYP2D6 variants that are, as yet, uncharacterized.

Due to time and cost limitations, phenotypic drug response variation due to the presence of CYP2D6 variants is not adequately characterized during clinical trials of pharmaceutical drugs, but is only fully characterized once the pharmaceutical drug is used by the general population. There is currently no adequate method of screening a population prior to administration of pharmaceutical drugs in the general population to identify CYP2D6 variants in the population predictive of phenotypes likely to result in adverse reactions.

Therefore, there is a need for a method of screening a population to identify CYP2D6 variants in the population. Further, there is a need for a method of predicting adverse reactions to a pharmaceutical drug that is metabolized by the Cytochrome p450 isoenzyme CYP2D6. Additionally, there is a need to identify all variants of the Cytochrome p450 isoenzyme CYP2D6 that cause altered pharmaceutical drugs metabolism.

SUMMARY

In one embodiment of the present invention, there is provided a primer set that can be used to screen a polynucleotide sample to detect and identify variants in the Cytochrome P450 isoenzyme 2D6 (CYP2D6) gene. The primer set comprises one or more than one primer group of the three primer groups of sequences selected from the primer groups consisting of Primer Group I (16 or more than 16 consecutive nucleotides of SEQ ID NO:9, 16 or more than 16 consecutive nucleotides of SEQ ID NO:10, 16 or more than 16 consecutive nucleotides of SEQ ID NO:11, 16 or more than 16 consecutive nucleotides of SEQ ID NO:12, 16 or more than 16 consecutive nucleotides of SEQ ID NO:13 and 16 or more than 16 consecutive nucleotides of SEQ ID NO:14); Primer Group II (16 or more than 16 consecutive nucleotides of SEQ ID NO:15, 16 or more than 16 consecutive nucleotides of SEQ ID NO:16; 16 or more than 16 consecutive nucleotides of SEQ ID NO:17, 16 or more than 16 consecutive nucleotides of SEQ ID NO:18, 16 or more than 16 consecutive nucleotides of SEQ ID NO:19, 16 or more than 16 consecutive nucleotides of SEQ ID NO:20, 16 or more than 16 consecutive nucleotides of SEQ ID NO:21, 16 or more than 16 consecutive nucleotides of SEQ ID NO:22, 16 or more than 16 consecutive nucleotides of SEQ ID NO:23 and 16 or more than 16 consecutive nucleotides of SEQ ID NO:24); and Primer Group III (16 or more than 16 consecutive nucleotides of SEQ ID NO:25; 16 or more than 16 consecutive nucleotides of SEQ ID NO:26; 16 or more than 16 consecutive nucleotides of SEQ ID NO:27, 16 or more than 16 consecutive nucleotides of SEQ ID NO:28, 16 or more than 16 consecutive nucleotides of SEQ ID NO:29, 16 or more than 16 consecutive nucleotides of SEQ ID NO:30, 16 or more than 16 consecutive nucleotides of SEQ ID NO:31, and 16 or more than 16 consecutive nucleotides of SEQ ID NO:32).

In one embodiment, the primer set comprises two primer groups selected from the group consisting of Primer Group I, Primer Group II and Primer Group III. In another embodiment, the primer set comprises all three primer groups Primer Group I, Primer Group II and Primer Group III. In one embodiment, each sequence consists of at least 17 consecutive nucleotides. In another embodiment, each sequence consists of at least 18 consecutive nucleotides. In another embodiment, each sequence consists of at least 19 consecutive nucleotides. In another embodiment, each sequence consists of at least 20 consecutive nucleotides. In another embodiment, each sequence consists of at least 21 consecutive nucleotides. In another embodiment, one or more than one sequence additionally comprises a tail sequence. In another embodiment, one or more than one sequence has one or more than one dUTP substituted for TTP.

In another embodiment of the present invention, there is provided a method of screening a polynucleotide sample to detect and identify the presence of one or more than one variant in the CYP2D6 gene in the sample. The method comprises a) providing a polynucleotide sample potentially comprising a sequence comprising at least about 50 consecutive nucleotides from one or more than one of the sequences of the wild type CYP2D6*1, SEQ ID NO:1, one or more than one variant of wild type CYP2D6*1, SEQ ID NO:1 or both wild type CYP2D6*1, SEQ ID NO:1 and one or more than one variant of wild type CYP2D6*1, SEQ ID NO:1; b) providing a primer set according to the present invention; c) amplifying the polynucleotide sample using the provided primer set to produce a set of amplicons; and d) analyzing the amplicons to identify the presence of one CYP2D6*1 gene, SEQ ID NO:1, the presence of one or more than one variant of the CYP2D6*1 gene, SEQ ID NO:1 or to identify one or more than one specific variant of the CYP2D6*1 gene, SEQ ID NO:1 in the sample.

In another embodiment of the present invention, there is provided a method of predicting the potential for altered metabolism of a substance, including one or more than one pharmaceutical drug, by a first individual compared to a second control individual, where the substance is metabolized by the CYP2D6 isoenzyme, and where the second control individual is homozygous for the wild type allele of the CYP2D6*1, SEQ ID NO:1. The method comprises a) providing a polynucleotide sample from the first individual; b) providing a primer set according to the present invention; c) amplifying the polynucleotide sample using the provided primer set to produce a set of amplicons; d) analyzing the amplicons to detect and identify one or more than one variant in the CYP2D6 gene from the first individual; and e) analyzing the one or more than one variant in the CYP2D6 gene detected and identified to determine if it constitutes a silent variant or non-silent variant; where the absence of a non-silent variant means that the first individual will not have the potential for altered metabolism of the substance, and where the presence of a non-silent variant means that the first individual will have the potential for altered metabolism of the substance.

In another embodiment of the present invention, there is provided a method of screening a population to detect and identify the presence of one or more than one variant in the CYP2D6 gene. The method comprises a) providing a plurality of polynucleotide samples from the population; b) providing a primer set according to the present invention; c) amplifying the polynucleotide sample using the provided primer set to produce a set of amplicons; and d) analyzing the amplicons to detect and identify of one or more than one variant of the CYP2D6*1 gene, SEQ ID NO:1 in the sample. In one embodiment, the plurality of polynucleotide samples is a plurality of random samples of individuals in the population. In another embodiment, the plurality of polynucleotide samples is one or more than one sample from each individual in the population. In another embodiment, the method of screening a population further comprises determining the distribution of the variants in the CYP2D6 gene in the population. In another embodiment, the method of screening a population further comprises recording the presence and identity, or recording the distribution of the variants in the CYP2D6 gene in the population sample, in writing or another suitable media.

In a preferred embodiment, amplifying the polynucleotide sample in a method of the present invention comprises using modified nucleotides. In a particularly preferred embodiment, the modified nucleotides are selected from the group consisting of deaza dATP, deaza dGTP, and nucleotides labeled with one or more than one label selected from the group consisting of biotin, digoxigenin, and a fluorescent dye.

In a preferred embodiment, amplifying the polynucleotide sample in a method of the present invention comprises using dUTP in place of TTP. In another preferred embodiment, the amplification step in a method of the present invention is performed in two stages. In another preferred embodiment, analyzing the amplicons in a method of the present invention is performed using a method selected from the group consisting of dideoxy sequencing, pyrosequencing and SSCP.

In another embodiment of the present invention, there is provided a kit for screening a polynucleotide sample to detect and identify the presence of one or more than one variant in the CYP2D6 gene in the sample, comprising suitable amounts of a primer set according to the present invention. In one embodiment, the kit further comprises one or more than one additional reagent or one or more than one vessel to amplify the polynucleotide sample, to analyze the amplicons, or both to amplify the polynucleotide sample and to analyze the amplicons. In a preferred embodiment, the additional reagent is selected from the group consisting of one or more than one DNA dependent polymerase, one or more than one buffer, one or more than one detergents and one or more than one stabilizing agent.

In another embodiment of the present invention, there is provided a purified or isolated variant of SEQ ID NO:1 having one or more than one of the alterations selected from the group consisting of C>T at position 1522, G insert at position 1576, G>C at position 1851, A>C at position 1852, A>G at position 1864, T>A at position 3230, C>T at position 3232, G>A at position 3335, C>T at position 3542, T>C at position 3617, A>G at position 3716, C>T at position 3922, G>T at position 4221, G>A at position 4280, G>A at position 4282, T>A at position 4379, T>C at position 4555, G>A at position 4607, C>T at position 4820, A>G at position 4854, T>C at position 4873, insert GT at position 4878, C>A at position 5003, T>C at position 5027, C>A at position 5054, C>T at position 5409, G>A at position 5496, C>T at position 5774, C>T at position 5791, C>T at position 5948, C>T at position 6020 and an exon 9 gene conversion.

In another embodiment of the present invention, there is provided a method of predicting the potential for altered metabolism of a substance, including one or more than one pharmaceutical drug, by a first individual compared to a second control individual, where the substance is metabolized by the CYP2D6 isoenzyme, and where the second control individual is homozygous for the wild type allele of the CYP2D6*1, SEQ ID NO:1. The method comprises a) detecting and identifying one or more than one variant in the CYP2D6 gene from the first individual; and b) analyzing the one or more than one variant in the CYP2D6 gene detected and identified to determine if it constitutes one or more than one variant according to the present invention; where the presence of the one or more than one variant means that the first individual will have the potential for altered metabolism of the substance.

In another embodiment of the present invention, there is provided a purified or isolated variant of SEQ ID NO:3 having one or more than one of the alterations selected from the group consisting of F>I at position 120, F>F at position 120, E>K at position 155, R>R at position 194, F>F at position 219, L>L at position 276, H>H at position 324, R>STOP at position 344, Y>C at position 355, H>H at position 361, V>FRAMESHIFT at position 363, E>K at position 418, H>Y at position 478, F>F at position 483.

In another embodiment of the present invention, there is provided a method of predicting the potential for altered metabolism of a substance, including one or more than one pharmaceutical drug, by a first individual compared to a second control individual, where the substance is metabolized by the CYP2D6 isoenzyme, and where the second control individual is homozygous for the wild type allele of the CYP2D6*1, SEQ ID NO:1. The method comprises a) detecting and identifying one or more than one variant in the CYP2D6 isoenzyme from the first individual; and b) analyzing the one or more than one variant in the CYP2D6 isoenzyme detected and identified to determine if it constitutes one or more than one variant according to the present invention; where the presence of the one or more than one variant means that the first individual will have the potential for altered metabolism of the substance.

DESCRIPTION

According to one embodiment of the present invention, there is provided a primer set that can be used to screen a polynucleotide sample to detect and identify variants in the Cytochrome P450 isoenzyme 2D6 (CYP2D6) gene. According to another embodiment of the present invention, there is provided a method of screening a polynucleotide sample to detect and identify the presence of one or more than one variant in the CYP2D6 gene in the sample. According to another embodiment of the present invention, there is provided a method of screening a population to detect and identify the presence of one or more than one variant in the CYP2D6 gene. According to another embodiment of the present invention, there is provided a method of predicting the potential for altered metabolism of a substance, including one or more than one pharmaceutical drug, by a first individual compared to a second individual, where the substance is metabolized by the CYP2D6 isoenzyme. According to another embodiment of the present invention, there is provided a kit for performing a method of the present invention. According to another embodiment of the present invention, there are provided novel purified and isolated variants of the Cytochrome p450 CYP2D6 gene and the CYP2D6 isoenzyme, including both silent variants and non-silent variants.

As used in this disclosure, the term "non-silent variant" refers to a CYP2D6 gene variant that causes a change in the production, regulation, length or sequence of the wild type CYP2D6 isoenzyme. As used in this disclosure, the term "silent variant" refers to a CYP2D6 gene variant that causes a change in the production, regulation, length or sequence of the wild type CYP2D6 isoenzyme. Both a non-silent variant and a silent variant can be the result of one or more than one point mutation that is a single nucleotide polymorphism, a deletion of one or more than one nucleotide, an insertion of one or more than one nucleotide, a gene conversion, or a combination of the preceding.

As used in this disclosure, the term "comprise" and variations of the term, such as "comprising" and "comprises," are not intended to exclude other additives, components, integers or steps.

The wild type allele of the CYP2D6 gene is designated as CYP2D6*1, GenBank accession number M33388, SEQ ID NO:1, and contains 9432 base pairs. The CYP2D6 gene is located on chromosome 22q13.1. The CYP2D6*1 gene, SEQ ID NO:1, is transcribed into an mRNA, GenBank accession number NM-000106, SEQ ID NO:2, that contains 9 exons, residues 1532–1799 of SEQ ID NO:1 (exon 1); residues 2503–2674 of SEQ ID NO:1 (exon 2); residues 3225–3377 of SEQ ID NO:1 (exon 3); residues 3466–3626 of SEQ ID NO:1 (exon 4); residues 4060–4236 of SEQ ID NO:1 (exon 5); residues 4427–4568 of SEQ ID NO:1 (exon 6); residues 4776–4963 of SEQ ID NO:1 (exon 7); residues 5418–5559 of SEQ ID NO:1 (exon 8); and residues 5658–5909 of SEQ ID NO:1 (exon 9). The CYP2D6 mRNA, SEQ ID NO:2, is translated into the wild type CYP2D6 isoenzyme, GenBank accession number AAA53500, SEQ ID NO:3, containing 497 amino acids.

There are a number of pseudogenes in the human genome on chromosome 22q close to the location of functional CYP2D6*1 gene, SEQ ID NO:1. These pseudogenes include GenBank accession number M33387, SEQ ID NO:4; GenBank accession number X58467, SEQ ID NO:5; GenBank accession number X58468, SEQ ID NO:6; GenBank accession number NG-000853, SEQ ID NO:7; and GenBank accession number NG-000854; SEQ ID NO:8. These pseudogenes can cause false positive results in tests for variants of the CYP2D6 gene.

In one embodiment, the present invention is a primer set that can be used to interrogate a polynucleotide sample to detect and identify variants in the Cytochrome P450 isoenzyme 2D6 (CYP2D6) gene, and thereby, to detect and identify variants in the Cytochrome P450 2D6 (CYP2D6) isoenzyme. The variants include differences in the sequence of the CYP2D6 gene that can affect the function of the translated CYP2D6 isoenzyme by changing the production, regulation, length or sequence of the CYP2D6 isoenzyme compared to the wild type CYP2D6 isoenzyme, and differences in the sequence of the CYP2D6 gene that code for 5' and 3' untranslated regions and for flanking intronic sequences that effect the production, regulation, length or sequence of the transcribed messenger RNA, and combinations of the preceding. The primer set permits amplification from a small polynucleotide sample of selected portions of the coding portion of the CYP2D6 gene, or amplification of the entire coding portion of the CYP2D6 gene, as well as the flanking intronic sequences that are relevant to recognition of splice sites. The primer set further permits the detection of genetic variants of the CYP2D6 gene without interference from pseudogenes, or from homologous or paralogous genes of non-CYP2D6 Cytochrome p450 genes. The primer set also permits the detection of low frequency variants that affect pharmaceutical drugs metabolism, thereby decreasing the false negative rate in variant screening.

TABLE I

EXAMPLES OF PRIMERS

| SEQ ID NO: | AMPLIFICATION REGION | AMPLIFICATION DIRECTION | SEQUENCE | AMPLICON SIZE | GROUP |
|---|---|---|---|---|---|
| 9 | EXON 1–2 | FORWARD | 5'AGCAGAGGGCAAAGGCCATCA | 1281 | I |
| 10 | EXON 1–2 | REVERSE | 5'CTCTCTGCCCAGCTCGGACTA | 1281 | I |
| 11 | EXON 1 | FORWARD | 5'CTTTATAAGGGAAGGGTCACG | 346 | I |
| 12 | EXON 1 | REVERSE | 5'AGGGGAGCCTCAGCACCTCTG | 346 | I |

TABLE I-continued

EXAMPLES OF PRIMERS

| SEQ ID NO: | AMPLIFICATION REGION | AMPLIFICATION DIRECTION | SEQUENCE | AMPLICON SIZE | GROUP |
|---|---|---|---|---|---|
| 13 | EXON 2 | FORWARD | 5'GGTGATCCTGGCTTGACAAGA | 251 | I |
| 14 | EXON 2 | REVERSE | 5'CCACGGAAATCTGTCTCTGTC | 251 | I |
| 15 | EXON 3–6 | FORWARD | 5'TGGTGGGGCTAATGCCTTCAT | 1559 | II |
| 16 | EXON 3–6 | REVERSE | 5'CCGGCCCCTGACACTCCTTCT | 1559 | II |
| 17 | EXON 3 | FORWARD | 5'GGTGGATGGTGGGGCTAATGC | 252 | II |
| 18 | EXON 3 | REVERSE | 5'CTTCCCAGTTCCCGCTTTGTG | 252 | II |
| 19 | EXON 4 | FORWARD | 5'ACGGGGAAGGCGACCCCTTAC | 242 | II |
| 20 | EXON 4 | REVERSE | 5'GAGCTCGCCCTGCAGAGACTC | 242 | II |
| 21 | EXON 5 | FORWARD | 5'AGAGCACAGGAGGGATTGAGA | 277 | II |
| 22 | EXON 5 | REVERSE | 5'ATTCCTCCTGGGACGCTCAAC | 277 | II |
| 23 | EXON 6 | FORWARD | 5'CCGTTCTGTCCCGAGTATGCT | 207 | II |
| 24 | EXON 6 | REVERSE | 5'CCCCTGCACTGTTTCCCAGAT | 207 | II |
| 25 | EXON 7–9 | FORWARD | 5'GGAGGCAAGAAGGAGTGTCAG | 1397 | III |
| 26 | EXON 7–9 | REVERSE | 5'ACCAATCTGGGCAGTCAGAGT | 1397 | III |
| 27 | EXON 7 | FORWARD | 5'GGCCGGACCCCTGGGTGCTG | 277 | III |
| 28 | EXON 7 | REVERSE | 5'GCTGGTGCTGAGCTGGGTGA | 277 | III |
| 29 | EXON 8 | FORWARD | 5'TAGAGTCCAGTCCCCACTCTC | 227 | III |
| 30 | EXON 8 | REVERSE | 5'AGACTCCACGGAAGGGGACAG | 227 | III |
| 31 | EXON 9 | FORWARD | 5'TCACCCAGGAGCCAGGCTCAC | 332 | III |
| 32 | EXON 9 | REVERSE | 5'TGATCCCAACGAGGGCGTGAG | 332 | III |

The primer set of the present invention comprises a plurality of primers selected from the group consisting of the primers shown in Table I. In a preferred embodiment, the present invention comprises one or more than one primer group of the three primer groups selected from the primer groups consisting of Primer Group I (SEQ ID NO:9, SEQ ID NO:10, SEQ ID NO:11, SEQ ID NO:12, SEQ ID NO:13 and SEQ ID NO:14); Primer Group II (SEQ ID NO:15, SEQ ID NO:16; SEQ ID NO:17, SEQ ID NO:18, SEQ ID NO:19, SEQ ID NO:20, SEQ ID NO:21, SEQ ID NO:22, SEQ ID NO:23 and SEQ ID NO:24); and Primer Group III (SEQ ID NO:25; SEQ ID NO:26; SEQ ID NO:27, SEQ ID NO:28, SEQ ID NO:29, SEQ ID NO:30, SEQ ID NO:31 and SEQ ID NO:32). In a preferred embodiment of the present invention, the primer set comprises two primer groups selected from the group consisting of Primer Group I, Primer Group II and Primer Group III. In a particularly preferred embodiment, the primer set comprises all three primer groups, Primer Group I, Primer Group II and Primer Group III.

Each primer, SEQ ID NO:9 through SEQ ID NO:32, is shown having exactly 21 nucleotides. However, as will be understood by those with skill in the art with reference to this disclosure, each primer can be truncated to contain less than 21 nucleotides. In one embodiment, one or more than one primer consists of only 16 consecutive nucleotides, only 17 consecutive nucleotides, only 18 consecutive nucleotides, only 19 consecutive nucleotides, or only 20 consecutive nucleotides of the sequences disclosed. Truncating the primer will usually decrease the binding efficiency of the primer and can cause less specific binding. Thus, in a preferred embodiment, the primer set comprises primers having the full sequences shown in Table I for maximum efficiency. However, truncated primers will usually still work in the methods of the present invention.

Additionally, primers from the primer set of the present invention can include added tail sequences, in particular at their 5' ends. Examples of suitable include −40 M13 Forward Promer, −21 M13 Forward Primer, −28 M13 Reverse Primer, −28 M13 Reverse 2 Primer, −29 M13 Reverse Primer, SP6 Primer, T7 Primer, T3 Primer, and Poly T (16–24 nucleotides) Primer. However, other tail sequences can also be used, as will be understood by those with skill in the art with reference to this disclosure. The addition of tail sequences is particularly preferred when the primers are truncated, in order to increase their binding efficiency as will be understood by those with skill in the art with reference to this disclosure. Further, dUTP can be substituted for TTP in a primer, as will be understood by those with skill in the art with reference to this disclosure.

Primer Group 1 is used to amplify the region of the CYP2D6 gene, SEQ ID NO:1, containing residues 1532–1799 of SEQ ID NO:1 (exon 1); and residues 2503–2674 of SEQ ID NO:1 (exon 2). Primer Group II is used to amplify the region of the CYP2D6 gene, SEQ ID NO:1, containing residues 3225–3377 of SEQ ID NO:1 (exon 3); residues 3466–3626 of SEQ ID NO:1 (exon 4); residues 4060–4236 of SEQ ID NO:1 (exon 5); and residues 4427–4568 of SEQ ID NO:1 (exon 6). Primer Group III is used to amplify the region of the CYP2D6 gene, SEQ ID NO:1, containing residues 4776–4963 of SEQ ID NO:1 (exon 7); residues 5418–5559 of SEQ ID NO:1 (exon 8); and residues 5658–5909 of SEQ ID NO:1 (exon 9).

In another embodiment, the present invention is a method of screening a polynucleotide sample to detect and identify the presence of one or more than one variant in the CYP2D6 gene in the sample. The method comprises, first, providing a polynucleotide sample potentially comprising a sequence comprising at least about 50 consecutive nucleotides from one or more than one of the sequences of the wild type CYP2D6*1, SEQ ID NO:1, one or more than one variant of wild type CYP2D6*1, SEQ ID NO:1 or both wild type CYP2D6*1, SEQ ID NO:1 and one or more than one variant of wild type CYP2D6*1, SEQ ID NO:1. The polynucleotide sample can originate from a human, a nonhuman animal including a transgenic animal or clone, or from another suitable source, as will be understood by those with skill in the art with reference to this disclosure. The polynucleotide sample can be in the form of one or more than one peripheral whole blood sample, buccal swab, Guthrie blood spot, preserved tissues sample such as a liver sample, paraffin embedded tissue, or from a clone library, or from another suitable source, as will be understood by those with skill in the art with reference to this disclosure.

Next, the method comprises providing a primer set according to the present invention. Then, the method comprises amplifying the polynucleotide sample using the provided primer set. Amplification can be performed using standard PCR, using the method as disclosed in U.S. Pat. No. 6,322,988 to Dawson et al, the contents of which are incorporated into this disclosure by reference in their entirety, or using another amplification method as will be understood by those with skill in the art with reference to this disclosure.

Additionally, as will be understood by those with skill in the art with reference to this disclosure, modified nucleotides, such as deaza dATP or deaza dGTP, can be used in the amplification step in conjunction with high denaturation temperatures, or for other reasons such as when the sequence of the CYP2D6 gene to be amplified contains high G/C or high A/T, and dUTP can be substituted for TTP. Further, modified bases in the form of their deoxynucleotide triphosphate can be used in the amplification step to introduce labels, such as biotin, digoxigenin or fluorescent dyes, such as fluoresceine, to produce labeled amplification products. The labeled amplification products can then be identified using array technology or can be used for other purposes, as will be understood by those with skill in the art with reference to this disclosure.

In a preferred embodiment, the amplification step is performed in two stages. The amplification step can be used to amplify a region of the CYP2D6 gene containing 1532–1799 of SEQ ID NO:1 (exon 1) and residues 2503–2674 of SEQ ID NO:1 (exon 2) using Primer Group I; or containing residues 3225–3377 of SEQ ID NO:1 (exon 3), residues 3466–3626 of SEQ ID NO:1 (exon 4), residues 4060–4236 of SEQ ID NO:1 (exon 5) and residues 4427–4568 of SEQ ID NO:1 (exon 6) using Primer Group II; or containing residues 4776–4963 of SEQ ID NO:1 (exon 7), residues 5418–5559 of SEQ ID NO:1 (exon 8) and residues 5658–5909 of SEQ ID NO:1 (exon 9) using Primer Group III; or containing 1532–1799 of SEQ ID NO:1 (exon 1), residues 2503–2674 of SEQ ID NO:1 (exon 2), residues 3225–3377 of SEQ ID NO:1 (exon 3), residues 3466–3626 of SEQ ID NO:1 (exon 4), residues 4060–4236 of SEQ ID NO:1 (exon 5) and residues 4427–4568 of SEQ ID NO:1 (exon 6) using Primer Group I and Primer Group II; or containing 1532–1799 of SEQ ID NO:1 (exon 1), residues 2503–2674 of SEQ ID NO:1 (exon 2), residues 4776–4963 of SEQ ID NO:1 (exon 7), residues 5418–5559 of SEQ ID NO:1 (exon 8) and residues 5658–5909 of SEQ ID NO:1 (exon 9) using Primer Group I and Primer Group III; or containing residues 3225–3377 of SEQ ID NO:1 (exon 3), residues 3466–3626 of SEQ ID NO:1 (exon 4), residues 4060–4236 of SEQ ID NO:1 (exon 5), residues 4427–4568 of SEQ ID NO:1 (exon 6), residues 4776–4963 of SEQ ID NO:1 (exon 7), residues 5418–5559 of SEQ ID NO:1 (exon 8) and residues 5658–5909 of SEQ ID NO:1 (exon 9) using Primer Group II and Primer Group III; or containing 1532–1799 of SEQ ID NO:1 (exon 1), residues 2503–2674 of SEQ ID NO:1 (exon 2), residues 3225–3377 of SEQ ID NO:1 (exon 3), residues 3466–3626 of SEQ ID NO:1 (exon 4), residues 4060–4236 of SEQ ID NO:1 (exon 5), residues 4427–4568 of SEQ ID NO:1 (exon 6), residues 4776–4963 of SEQ ID NO:1 (exon 7), residues 5418–5559 of SEQ ID NO:1 (exon 8) and residues 5658–5909 of SEQ ID NO:1 (exon 9) using Primer Group I, Primer Group II and Primer Group III. In a preferred embodiment, the amplification step is used to amplify a region of the CYP2D6 gene containing 1532–1799 of SEQ ID NO:1 (exon 1), residues 2503–2674 of SEQ ID NO:1 (exon 2), residues 3225–3377 of SEQ ID NO:1 (exon 3), residues 3466–3626 of SEQ ID NO:1 (exon 4), residues 4060–4236 of SEQ ID NO:1 (exon 5), residues 4427–4568 of SEQ ID NO:1 (exon 6), residues 4776–4963 of SEQ ID NO:1 (exon 7), residues 5418–5559 of SEQ ID NO:1 (exon 8) and residues 5658–5909 of SEQ ID NO:1 (exon 9) using Primer Group I, Primer Group II and Primer Group III.

Though the amplification step will now be disclosed in the context of using all three primer groups, Primer Group I, Primer Group II and Primer Group III, to amplify regions of the CYP2D6 gene containing 1532–1799 of SEQ ID NO:1 (exon 1), residues 2503–2674 of SEQ ID NO:1 (exon 2), residues 3225–3377 of SEQ ID NO:1 (exon 3), residues 3466–3626 of SEQ ID NO:1 (exon 4), residues 4060–4236 of SEQ ID NO:1 (exon 5), residues 4427–4568 of SEQ ID NO:1 (exon 6), residues 4776–4963 of SEQ ID NO:1 (exon 7), residues 5418–5559 of SEQ ID NO:1 (exon 8) and residues 5658–5909 of SEQ ID NO:1 (exon 9), amplifying shorter regions of the CYP2D6 gene can be performed with corresponding procedures using either one primer group or two primer groups, as will be understood by those with skill in the art with reference to this disclosure.

In the first amplification stage, three regions of the CYP2D6 gene are amplified using the six primers, SEQ ID NO:9, SEQ ID NO:10, SEQ ID NO:15, SEQ ID NO:16, SEQ ID NO:25 and SEQ ID NO:26. The first amplification stage can be performed, for example, using standard PCR as follows, though other methods can also be used as will be understood by those with skill in the art with reference to this disclosure. By way of example only, first, a sample of 1 µl of 1×T.E. buffer containing 20 ng of a polynucleotide sample is provided potentially comprising at least 50 consecutive nucleotides from one or more than one sequence selected from the group consisting of the wild type CYP2D6*1, SEQ ID NO:1, one or more than one variant of wild type CYP2D6*1, SEQ ID NO:1 and both the wild type CYP2D6*1, SEQ ID NO:1 and one or more than one variant of wild type CYP2D6*1, SEQ ID NO:1. Then, 19 µl of buffer is added to the polynucleotide sample. The 19 µl of buffer contains 0.2–2.0 units of Taq Gold, 200 µM each of dATP, dCTP, dGTP and TTP, 2 mM MgCl$_2$, 50 mM KCl, 5 mM dithiothreitol 2% DMSO, 10 mM TRIS/TRIS HCl, pH 9.0, and 10 pMoles of one primer pair selected from the group consisting of SEQ ID NO:9 and SEQ ID NO:10; SEQ ID NO:15 and SEQ ID NO:16; and SEQ ID NO:25 and SEQ ID NO:26. The buffered polynucleotide sample is then thermocycled using a standard thermocycler and standard vessels, and using a first cycle of 95° C. for 12 minutes to activate the Taq Gold, followed by 30–40 cycles consisting of denaturation at 95° C. for 30 seconds, annealing at 62° C. for 30 seconds, extension at 72° C. for 2 minutes, and a final extension at 72° C. for 8 minutes. Then, the amplification is repeated twice more on the same sample using each additional primer pair of the three primer pairs until the sample has been amplified using all three primer pairs. In a preferred embodiment, the first amplification stage is performed using two of the three primer pairs simultaneously, rather than sequentially, following by an amplification using the third primer pair. In a particularly preferred embodiment, the amplification is performed using all three primer pairs simultaneously. Performing the amplification using each of the three primer pairs sequentially rather than simultaneously is particularly preferred if the analysis method to be used to sequence the amplicons disclosed below, such as SSCP, would function less optimally on the amplicons produced by all three primer pairs simultaneously, as will be understood by those with skill in the art with reference to this disclosure. This first amplification stage results in a sample comprising three amplicons containing 1532–1799 of SEQ ID NO:1 exons 1–2; exons 3–6; and exons 7–9, as well as the four flanking intronic sequences that effect the production, regulation, length or sequence of the transcribed messenger RNA (or in a sample comprising one or two of these amplicons and flaking intronic sequences, if less than all three primer pairs are used in the first amplification stage, as will be understood by those with skill in the art with reference to this disclosure).

Next, the sample comprising the amplicons resulting from the first amplification stage is subjected to a second amplification stage using some or all of the 18 remaining primers from the primer set of the present invention; SEQ ID NO:11 through SEQ ID NO:14, SEQ ID NO:17 through SEQ ID NO:24, and SEQ ID NO:27 through SEQ ID NO:32. First, 1 µl of sample resulting from the first amplification stage is diluted 1:1000 in 0.1×T.E. buffer. Then, 19 µl of buffer is added to the diluted sample. The 19 µl of buffer contains 0.2–2.0 units of Taq Gold, 200 µM each of dATP, dCTP, dGTP and TTP, 2 mM MgCl$_2$, 50 mM KCl, 5 mM dithiothreitol 2% DMSO, 10 mM TRIS/TRIS HCl, pH 9.0, and 10 pMoles each of one or more than one primer pair, depending on the exon or exons of interest as follows: SEQ ID NO:11 and SEQ ID NO:12 for 1532–1799 of SEQ ID NO:1 (exon 1); SEQ ID NO:13 and SEQ ID NO:14 for residues 2503–2674 of SEQ ID NO:1 (exon 2); SEQ ID NO:17 and SEQ ID NO:18 for residues 3225–3377 of SEQ ID NO:1 (exon 3); SEQ ID NO:19 and SEQ ID NO:20 for residues 3466–3626 of SEQ ID NO:1 (exon 4); SEQ ID NO:21 and SEQ ID NO:22 for residues 4060–4236 of SEQ ID NO:1 (exon 5); SEQ ID NO:23 and SEQ ID NO:24 for residues 4427–4568 of SEQ ID NO:1 (exon 6); SEQ ID NO:27 and SEQ ID NO:28 for residues 4776–4963 of SEQ ID NO:1 (exon 7); SEQ ID NO:29 and SEQ ID NO:30 for residues 5418–5559 of SEQ ID NO:1 (exon 8); or SEQ ID NO:31 and SEQ ID NO:32 for residues 5658–5909 of SEQ ID NO:1 (exon 9), as will be understood by those with skill in the art with reference to this disclosure. The sample is then thermocycled using a standard thermocycler and standard vessels, and using a first cycle of 95° C. for 12 minutes to activate the Taq Gold, followed by 30–40 cycles consisting of denaturation at 95° C. for 30 seconds, annealing at 62° C. for 30 seconds, extension at 72° C. for 2 minutes, and a final extension at 72° C. for 8 minutes. Then, the one or more than one primer pair used depends on the amplicons in the sample that resulted from the first amplification stage. If, for example, all three primer pairs, SEQ ID NO:9, SEQ ID NO:10, SEQ ID NO:15, SEQ ID NO:16, SEQ ID NO:25 and SEQ ID NO:26, were used in the first amplification stage, and the amplicons of interest include all 9 exons, then all remaining nine primer pairs are used in the second amplification stage. If only one or only two primer pairs were used in the first amplification stage, then fewer than all nine remaining primer pairs can be used in the second amplification stage, as will be understood by those with skill in the art with reference to this disclosure. In a preferred embodiment, the second amplification stage is performed using all nine primer pairs, SEQ ID NO:11 through SEQ ID NO:14, SEQ ID NO:17 through SEQ ID NO:24, and SEQ ID NO:27 through SEQ ID NO:32, simultaneously. In another preferred embodiment, the second amplification stage is performed using all nine primer pairs but where one or more than one of the nine primer pairs are used sequentially rather than simultaneously. When all nine primer pairs are used in the second amplification stage after a first amplification stage involving three primer pairs, the second amplification results in nine amplicons, each amplicon containing one exon as well as the four flanking intronic sequences that affect the production, regulation, length or sequence of the transcribed messenger RNA (or in fewer than nine amplicons and flaking intronic sequences if less than all eighteen primer pairs are used in the second amplification stage, as will be understood by those with skill in the art with reference to this disclosure).

The amplicons produced using the present method represent polynucleotides distinct from CYP2D6 pseudogenes, and from homologous or paralogous genes related to the CYP2D6 gene, thereby eliminating these sources of potential false positive results of the presence of variants. Further, since the present method amplifies only exons and their adjacent flanking intronic sequences, the method produces amplicons that are relevant to identifying only variants of the CYP2D6 gene having an effect of the CYP2D6 isoenzyme, SEQ ID NO:3.

Next, the method comprises analyzing the amplicons produced in the second amplification stage to identify the presence of CYP2D6*1 gene, SEQ ID NO:1, the presence of a variant of the CYP2D6*1 gene, SEQ ID NO:1 or to identify the specific variant of the CYP2D6*1 gene, SEQ ID NO:1 in the sample. This analysis step can be performed using any suitable method, such as dideoxy sequencing, pyrosequencing, SSCP or another suitable method, as will be understood by those with skill in the art with reference to this disclosure.

According to another embodiment of the present invention, there is provided a method of screening a population to detect and identify the presence of one or more than one variant in the CYP2D6 gene. The method comprises providing a plurality of polynucleotide samples from the population, where the plurality of polynucleotide samples is selected from a representative group of individuals from the population, such as for example, a plurality of random samples of individuals in the population or one or more than one sample from each individual in the population. Next, each of the pluralities of polynucleotide samples is subjected to a method of screening a polynucleotide sample to detect and identify the presence of one or more than one variant in the CYP2D6 gene in the polynucleotide sample according to the present invention. In a preferred embodiment, the method further comprises determining the distribution of the variants in the CYP2D6 gene in the population. In another preferred embodiment, the method comprises recording the presence and identity, or recording the distribution of the variants in the CYP2D6 gene in the population sample, in writing or another suitable media.

According to another embodiment of the present invention, there is provided a method of predicting the potential for altered metabolism of a substance, including one or more than one pharmaceutical drug, by a first individual compared to a second control individual, where the substance is metabolized by the CYP2D6 isoenzyme, and where the second control individual is homozygous for the wild type allele of the CYP2D6*1, SEQ ID NO:1. In one embodiment, the method comprises, first, providing a polynucleotide sample from the first individual. Next, the polynucleotide sample from the first individual is subjected to a method of screening a polynucleotide sample to detect and identify the presence of one or more than one variant in the CYP2D6 gene in the polynucleotide sample according to the present invention. Then, the one or more than one variant in the CYP2D6 gene detected and identified is analyzed to determine if it constitutes a silent variant or non-silent variant, where the absence of a non-silent variant means that the first individual will not have the potential for altered metabolism of the substance, and where the presence of a non-silent variant means that the first individual will have the potential for altered metabolism of the substance.

According to another embodiment of the present invention, there are provided novel purified and isolated variants of the Cytochrome p450 CYP2D6 gene and corresponding variants in the CYP2D6 isoenzyme, including both silent variants and non-silent variants. The variants were detected and identified using the methods of the present invention. The variants are disclosed in Table II. Further, some individuals had a plurality of the variants listed in Table I. The present invention, therefore, includes both the 32 variants of the Cytochrome p450 CYP2D6 gene and corresponding variants in the CYP2D6 isoenzyme, if any, as well as variants of the Cytochrome p450 CYP2D6 gene having a plurality of the variants listed in Table I, and corresponding variants in the CYP2D6 isoenzyme, if any.

TABLE II

VARIANTS OF THE CYTOCHROME P450 CYP2D6 GENE AND CORRESPONDING VARIANTS IN THE CYP2D6 ISOENZYME

| VARIANT NUMBER | POSITION CHANGE IN WILD TYPE SEQUENCE, SEQ ID NO:1 | POSITION CHANGE IN WILD TYPE SEQUENCE, SEQ ID NO:1, NUMBERED FROM ATG (MET) | VARIANT | POSITION CHANGE IN WILD TYPE POLYPEPTIDE SEQUENCE, SEQ ID NO:3 | VARIANT |
|---|---|---|---|---|---|
| 1 | 1522 | −98 | C > T | | |
| 2 | 1576 | −44 | insert GUIDING TUBE | | |
| 3 | 1851 | 232 | G > C | | |
| 4 | 1852 | 233 | A > C | | |
| 5 | 1864 | 245 | A > G | | |
| 6 | 3230 | 1611 | T > A | 120 | F > I |
| 7 | 3232 | 1613 | C > T | 120 | F > F |
| 8 | 3335 | 1716 | G > A | 155 | E > K |
| 9 | 3542 | 1923 | C > T | 194 | R > R |
| 10 | 3617 | 1998 | T > C | 219 | F > F |
| 11 | 3716 | 2097 | A > G | | |
| 12 | 3922 | 2303 | C > T | | |
| 13 | 4221 | 2602 | G > T | 276 | L > L |
| 14 | 4280 | 2661 | G > A | | |
| 15 | 4282 | 2663 | G > A | | |
| 16 | 4379 | 2760 | T > A | | |
| 17 | 4555 | 2936 | T > C | 324 | H > H |
| 18 | 4607 | 2988 | G > A | | |
| 19 | 4820 | 3201 | C > T | 344 | R > STOP |
| 20 | 4854 | 3235 | A > G | 355 | Y > C |
| 21 | 4873 | 3254 | T > C | 361 | H > H |
| 22 | 4878 | 3259 | insert GT | 363 | V > FRAME SHIFT |
| 23 | 5003 | 3384 | C > A | | |
| 24 | 5027 | 3408 | T > C | | |
| 25 | 5054 | 3435 | C > A | | |
| 26 | 5409 | 3790 | C > T | | |
| 27 | 5496 | 3877 | G > A | 418 | E > K |
| 28 | 5774 | 4155 | C > T | 478 | H > Y |
| 29 | 5791 | 4172 | C > T | 483 | F > F |
| 30 | 5948 | 4329 | C > T | | |
| 31 | 6020 | 4401 | C > T | | |
| 32 | EXON9 | | GENE CONVERSION | | |

According to another embodiment of the present invention, there is provided a method of predicting the potential for altered metabolism of a substance, including one or more than one pharmaceutical drug, by a first individual compared to a second control individual, where the substance is metabolized by the CYP2D6 isoenzyme, and where the second control individual is homozygous for the wild type allele of the CYP2D6*1, SEQ ID NO:1. In one embodiment, the method comprises, first, providing a polynucleotide sample from the first individual. Next, the polynucleotide sample from the first individual is subjected to a method of screening a polynucleotide sample to detect and identify the presence of one or more than one variant in the CYP2D6 gene in the polynucleotide sample according to the present invention. Then, the one or more than one variant in the CYP2D6 gene detected and identified is analyzed to determine if it constitutes one of the novel non-silent variants of the present invention, where the presence of one of the novel non-silent variants of the present invention means that the first individual will have the potential for altered metabolism of the substance.

In another embodiment, the present invention is a kit for performing a method of the present invention. The kit comprises suitable amounts of one or more than one primer group selected from the group consisting of Primer Group I, Primer Group II and Primer Group III to perform the amplification step of a method of the present invention. In one embodiment, the kit comprises suitable amounts of two primer groups selected from the group consisting of Primer Group I and Primer Group II; and Primer Group I and Primer Group III; and Primer Group II and Primer Group III. In a preferred embodiment, the kit comprises suitable amounts of all three primer groups Primer Group I, Primer Group II and Primer Group III. Additionally, the kit can comprise additional reagents or vessels for performing a method of the present invention, such as one or more than one DNA dependent polymerase, one or more than one buffer, one or more than one detergents and one or more than one stabilizing agent. Further, the kit can comprise reagents or vessels for analyzing or sequencing the amplicons resulting from a method of the present invention. Additionally, the kit can comprise written or recorded directions for performing a method of the present invention.

EXAMPLE

Method of Screening a Polynucleotide Sample to Detect and Identify the Presence of One or More than One Variant in the CYP2D6 Gene in the Sample A polynucleotide sample was screened to detect and identify the presence of one or more than one variant in the CYP2D6 gene in the sample according to the present invention as follows. First, polynucleotide samples were provided that potentially comprises a sequence comprising at least about 50 consecutive nucleotides from one or more than one of the sequences of the wild type CYP2D6*1, SEQ ID NO:1, one or more than one variant of wild type CYP2D6*1, SEQ ID NO:1 or both wild type CYP2D6*1, SEQ ID NO:1 and one or more than one variant of wild type CYP2D6*1, SEQ ID NO:1. The polynucleotide samples provided were human diversity panels of genomic DNA obtained from Corriel Laboratories. The panels consisted of 10 μg of genomic DNA each from a first group of 100 African Americans, a second group of 10 African Americans, 100 Caucasians, 10 Chinese Asians, 10 Japanese Asians, 10 non-Chinese, non-Japanese Asians, and 20 aged controls. Next, the samples were dried in a SpeedVac™ (Thermo Savant, Inc., Holbrook, N.Y. US) and then, resuspended in 1×T.E. buffer (1×T.E.=1 mM EDTA, 10 mM TrisHCl) having a pH 7.6 to a concentration of 200 ng/μl per sample. Stock samples were stored at −20° C. until ready for dispensing.

Once the samples were ready for dispensing, the samples were thawed and allowed to come to room temperature. Then, the samples were further diluted with 0.1×T.E. to a concentration of 2 ng/μl. The samples were then dispensed in 10 μl increments to individual wells of 96 well 200 μl PCR plates. The plated samples were then dried in an oven at between 60° C. and 70° C. for one hour until no visible moisture was observed in the wells of the plates. The dried samples in plates were then stored with a desiccant at room temperature in sealed containers until ready for amplification.

Next, the samples were subjected to a two-stage amplification procedure according to the present invention, using PCR. First, 20 μl of a master mix was added to each well. The master mix consisted of an aqueous buffer of 0.25 units of TAQ Gold™ (PE Applied Biosystems, Inc. Foster City, Calif. US), 2 mM $MgCl_2$, 50 mM KCl, 10 mM TrisHCl, pH 9.0 and 10 pMoles of each primer of the six primers, SEQ ID NO:9, SEQ ID NO:10, SEQ ID NO:15, SEQ ID NO:16, SEQ ID NO:25 and SEQ ID NO:26 as appropriate for the specific region of the CYP2D6 gene being amplified. The first amplification stage was conducted on thermocyclers (MJ Research, Inc., Cambridge, Mass. US) using a set of cycles consisting of 95° C. for 12 minutes, followed by a cycle consisting of denaturation at 95° C. for 30 seconds, a cycle of annealing at 60° C. for 20 seconds, and cycles of extension at 72° C. for 1 minute and 40 seconds. These three steps of cycling were repeated 34 additional times followed by a final cycle of extension at 72° C. for 8 minutes.

Then, 2 μl of the resulting amplicons were electrophoresed on 1% precast agarose gel containing ethidium bromide. The amplicons were stored at −20° C. until the second amplification stage.

Next, the amplicons from the first amplification stage were subjected to a second amplification stage. First, the amplicons were treated with ExoSap® (USB Corporation, Cleveland, Ohio US) using 1 μl of the enzyme mixture added directly to the amplicons in the wells of the 96 well plate in which they were originally subjected to the first amplification stage, and the plated amplicons were heated for 1 hour at 37° C., followed by heat inactivation at 65° C. for 30 minutes, followed by heating at 80° C. for 10 minutes, and then followed by cooling to 4° C.

One group of the ExoSap® treated samples were amplified using components from a core cycle sequencing kit (PE Applied Biosystems, Inc., Foster City, Calif. US). The amplification reaction was performed on 20 μl of substrate comprising the 2 μl treated sample (containing about 100 ng of amplicons), 10 pMoles each of exon specific primer pairs according to the present invention, (SEQ ID NO:11 through SEQ ID NO:14, SEQ ID NO:17 through SEQ ID NO:24, and SEQ ID NO:27 through SEQ ID NO:32), 2 units of FS polymerase, 4 μl of 5× reaction buffer and 1 μl each of the A and C terminator mixes, with the balance consisting of 18 megaohm water. The amplification reactions were performed in the wells of a 96 well PCR plate or in 200 μl PCR strip tubes (Fisher Scientific L.L.C., Pittsburgh, Pa. US) using cycling conditions consisting of a first denaturation step of 95° C. for 5 minutes, followed by 35 cycles of three steps consisting of heating at 95° C. for 30 seconds, annealing at 55° C. for 20 seconds, and extension at 60° C. for 4 minutes, followed by cooling to 4° C. Reactions were then cleaned to remove unincorporated terminators using a microtiter cleanup system (Millipore Corporation, Bedford, Mass. US).

The recovered 20 µl filtrates were then dried in the wells of a fresh 96 well plate under vacuum at 60° C. in a SpeedVac™ after the addition of 1 µl and a tetramethylrhodamine labeled MapMarker® TMR 650 (BioVentures, Inc., Murfreesboro, Tenn. US). The dried products were resuspended in 3 µl of 18 megaohm water and 3 µl of a mix of deionized formamide (American Bioanalytical Products, Natick, Mass. US). Next, the samples were denatured and concentrated to about 3 µl by heating at 95° C. for 10 minutes without an evaporation barrier and then cooled to 4° C.

1.2 µl of the denatured and concentrated samples were loaded onto individual teeth of a 50 tooth gel loading comb (The Gel Company, San Francisco, Calif. US) and then loaded onto the gels of an ABI Prism 377 DNA Sequencer (PE Applied Biosystems, Inc. Foster City, Calif. US) using the comb manufacturer's suggested protocol. The terminated polynucleotide fragments were analyzed on 0.2 mm thick 36 cm denaturing Long Ranger® polyacrylamide gels (FMC Corporation, Philadelphia, Pa. US) prepared using the instrument manufacturer's and the gel manufacturer's instructions. The gels were prepared 18 hours prior to use to assure complete polymerization of the acrylamide. The run conditions utilized were those recommended by the instrument manufacturer for performing dye terminated sequencing reactions for the core kit.

Sequencing reactions were also performed using 1 µl of sample (comprising about 50 ng of amplicons) of the treated PCR products and components from a Big Dye sequencing kit (PE Applied Biosystems, Inc. Foster City, Calif. US) setting up separate forward and reverse sequencing reactions using the exon specific forward or reverse primers, (SEQ ID NO:11 through SEQ ID NO:14, SEQ ID NO:17 through SEQ ID NO:24, and SEQ ID NO:27 through SEQ ID NO:32), according to the present invention specific for the region being sequenced. Modifications were made to the manufacturer's suggested protocol consisting of reducing the primer concentrations to 2.4 pMoles per reaction and using 4 µl of the supplied Ready Reaction Mix™ for each 20 µl reaction. Cycle sequencing was performed in 96 well plates using the recommended thermocycling conditions on a thermocycler. The reaction components were then cleaned to remove unincorporated terminators using a microtiter cleanup system.

Following the sequencing reaction, the terminated products were obtained by precipitation using the manufacturer's suggested procedure. The dried fragments obtained by this procedure were resuspended in 3 µl of 18 megaohm water and 3 µl of formamide. Samples were denatured uncapped at 95° C. for 10 minutes which reduced volume to about 3 µl. 1.2 µl of each sample was loaded onto the teeth of a 50-lane loading comb following manufacturer's protocol. Terminated fragments were electrophoresed on an ABI Prism 377 DNA Sequencer using the manufacturer's recommended procedure using 0.2 mm thick Long Ranger® polyacrylamide gels.

The sequence data obtained from both sequencing procedures were analyzed using fragment analysis software and compared to sequence data for the wild type CYP2D6*1 gene sequence, SEQ ID NO:1. The data obtained from the procedures revealed a plurality of variants of the CYP2D6 gene present in the samples that were not previously reported, especially in samples from Asians and African Americans.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A primer set that can be used to screen a polynucleotide sample to detect and identify variants in the Cytochrome P450 isoenzyme 2D6 (CYP2D6) gene comprising Primer Group II (16 or more than 16 consecutive nucleotides of SEQ ID NO:15, 16 or more than 16 consecutive nucleotides of SEQ ID NO:16; 16 or more than 16 consecutive nucleotides of SEQ ID NO:17, 16 or more than 16 consecutive nucleotides of SEQ ID NO:18, 16 or more than 16 consecutive nucleotides of SEQ ID NO:19, 16 or more than 16 consecutive nucleotides of SEQ ID NO:20, 16 or more than 16 consecutive nucleotides of SEQ ID NO:21, 16 or more than 16 consecutive nucleotides of SEQ ID NO:22, 16 or more than 16 consecutive nucleotides of SEQ ID NO:23 and 16 or more than 16 consecutive nucleotides of SEQ ID NO:24).

2. The primer set of claim 1, further comprising either Primer Group I (16 or more than 16 consecutive nucleotides of SEQ ID NO:9, 16 or more than 16 consecutive nucleotides of SEQ ID NO:10, 16 or more than 16 consecutive nucleotides of SEQ ID NO:11, 16 or more than 16 consecutive nucleotides of SEQ ID NO:12, 16 or more than 16 consecutive nucleotides of SEQ ID NO:13 and 16 or more than 16 consecutive nucleotides of SEQ ID NO:14); Primer Group III (16 or more than 16 consecutive nucleotides of SEQ ID NO:25; 16 or more than 16 consecutive nucleotides of SEQ ID NO:26; 16 or more than 16 consecutive nucleotides of SEQ ID NO:27, 16 or more than 16 consecutive nucleotides of SEQ ID NO:28, 16 or more than 16 consecutive nucleotides of SEQ ID NO:29, 16 or more than 16 consecutive nucleotides of SEQ ID NO:30, 16 or more than 16 consecutive nucleotides of SEQ ID NO:31, and 16 or more than 16 consecutive nucleotides of SEQ ID NO:32).

3. The primer set of claim 1, further comprising both Primer Group I (16 or more than 16 consecutive nucleotides of SEQ ID NO:9, 16 or more than 16 consecutive nucleotides of SEQ ID NO:10, 16 or more than 16 consecutive nucleotides of SEQ ID NO:11, 16 or more than 16 consecutive nucleotides of SEQ ID NO:12, 16 or more than 16 consecutive nucleotides of SEQ ID NO:13 and 16 or more than 16 consecutive nucleotides of SEQ ID NO:14); and Primer Group III (16 or more than 16 consecutive nucleotides of SEQ ID NO:25; 16 or more than 16 consecutive nucleotides of SEQ ID NO:26; 16 or more than 16 consecutive nucleotides of SEQ ID NO:27, 16 or more than 16 consecutive nucleotides of SEQ ID NO:28, 16 or more than 16 consecutive nucleotides of SEQ ID NO:29, 16 or more than 16 consecutive nucleotides of SEQ ID NO:30, 16 or more than 16 consecutive nucleotides of SEQ ID NO:31, and 16 or more than 16 consecutive nucleotides of SEQ ID NO:32).

4. The primer set of claim 1, where each sequence consists of at least 17 consecutive nucleotides.

5. The primer set of claim 1, where each sequence consists of at least 18 consecutive nucleotides.

6. The primer set of claim 1, where each sequence consists of at least 19 consecutive nucleotides.

7. The primer set of claim 1, where each sequence consists of at least 20 consecutive nucleotides.

8. The primer set of claim 1, where each sequence consists of at least 21 consecutive nucleotides.

9. The primer set of claim 1, where one or more than one sequence additionally comprises a tail sequence.

10. The primer set of claim 1, where one or more than one sequence has one or more than one dUTP substituted for TTP.

11. A method of screening a polynucleotide sample to detect and identity the presence of one or more than one variant in the CYP2D6 gene in the sample, comprising:
a) providing a polynucleotide sample potentially comprising a sequence comprising at least about 50 consecutive nucleotides from one or more than one of the sequences of the wild type CYP2D6*1, SEQ ID NO:1, one or more than one variant of wild type CYP2D6*1, SEQ ID NO:1 or both wild type CYP2D6*1, SEQ ID NO:1 and one or more than one variant of wild type CYP2D6*1, SEQ ID NO:1;
b) providing a primer set according to claim 1;
c) amplifying the polynucleotide sample using the provided primer set to produce a set of amplicons; and
d) analyzing the amplicons to identify the presence of CYP2D6*1 gene, SEQ ID NO:1, the presence of one or more than one variant of the CYP2D6*1 gene, SEQ ID NO:1 or to identify one or more than one specific variant of the CYP2D6*1 gene, SEQ ID NO:1 in the sample.

12. A method of screening a population to detect and identify the presence of one or more than one variant in the CYP2D6 gene, comprising:
a) providing a plurality of polynucleotide samples from the population;
b) providing a primer set according to claim 1;
c) amplifying the polynucleotide sample using the provided primer set to produce a set of amplicons; and
d) analyzing the amplicons to detect and identify one or more than one variant of the CYP2D6*1 gene, SEQ ID NO:1 in the sample.

13. The method of claim 12, where the plurality of polynucleotide samples is a plurality of random samples of individuals in the population.

14. The method of claim 12, where the plurality of polynucleotide samples is one or more than one sample from each individual in the population.

15. The method of claim 12, where the method of screening a population further comprises determining the distribution of the variants in the CYP2D6 gene in the population.

16. The method of claim 12, where the method of screening a population further comprises recording the presence and identity, or recording the distribution of the variants in the CYP2D6 gene in the population sample, in writing or another suitable media.

17. The method of claim 11 or 12, where amplifying the polynucleotide sample comprises using modified nucleotides.

18. The method of claim 11 or 12, where the modified nucleotides are selected from the group consisting of deaza dATP, deaza dGTP, and nucleotides labeled with one or more than one label selected from the group consisting of biotin, digoxigenin, and a fluorescent dye.

19. The method of claim 11 or 12, where amplifying the polynucleotide sample comprises using dUTP in place of TTP.

20. The method of claim 11 or 12, where the amplification step is performed in two stages.

21. The method of claim 11 or 12, where analyzing the amplicons is performed using a method selected from the group consisting of dideoxy sequencing, pyrosequencing and SSCP.

22. A kit for screening a polynucleotide sample to detect and identity the presence of one or more than one variant in the CYP2D6 gene in the sample, comprising suitable amounts of a primer set according to claim 1.

23. The kit of claim 22, further comprising one or more than one additional reagent or one or more than one vessel to amplify the polynucleotide sample, to analyze the amplicons, or both to amplify the polynucleotide sample and to analyze the amplicons.

24. The kit of claim 23, where the additional reagent is selected from the group consisting of one or more than one DNA dependent polymerase, one or more than one buffer, one or more than one detergent and one or more than one stabilizing agent.

25. A purified or isolated variant of SEQ ID NO:1 having a C>T substitution at position 1522.

26. A method of screening a polynucleotide sample to detect and identify the presence of one or more than one variant in the CYP2D6 gene in the sample, comprising:
a) providing a polynucleotide sample potentially comprising a sequence comprising at least about 50 consecutive nucleotides from one or more than one of the sequences of the wild type CYP2D6*1, SEQ ID NO:1, one or more than one variant of wild type CYP2D6*1, SEQ ID NO:1 or both wild type CYP2D6*1, SEQ ID NO:1 and one or more than one variant of wild type CYP2D6*1, SEQ ID NO:1;
b) providing a primer set according to claim 2;
c) amplifying the polynucleotide sample using the provided primer set to produce a set of amplicons; and d) analyzing the amplicons to identify the presence of CYP2D6*1 gene, SEQ ID NO: 1, the presence of one or more than one variant of the CYP2D6*1 gene, SEQ ID NO:1 or to identify one or more than one specific variant of the CYP2D6*1 gene, SEQ ID NO:1 in the sample.

27. A method of screening a population to detect and identify the presence of one or more than one variant in the CYP2D6 gene, comprising:
    a) providing a plurality of polynucleotide samples from the population;
    b) providing a primer set according to claim 2;
    c) amplifying the polynucleotide sample using the provided primer set to produce a set of amplicons; and
    d) analyzing the amplicons to detect and identify one or more than one variant of the CYP2D6*1 gene, SEQ ID NO:1 in the sample.

28. The method of claim 27, where the plurality of polynucleotide samples is a plurality of random samples of individuals in the population.

29. The method of claim 27, where the plurality of polynucleotide samples is one or more than one sample from each individual in the population.

30. The method of claim 27, where the method of screening a population further comprises determining the distribution of the variants in the CYP2D6 gene in the population.

31. The method of claim 27, where the method of screening a population further comprises recording the presence and identity, or recording the distribution of the variants in the CYP2D6 gene in the population sample, in writing or another suitable media.

32. The method of claim 26 or 27, where amplifying the polynucleotide sample comprises using modified nucleotides.

33. The method of claim 26 or 27, where the modified nucleotides are selected from the group consisting of deaza dATP, deaza dGTP, and nucleotides labeled with one or more than one label selected from the group consisting of biotin, digoxigenin, and a fluorescent dye.

34. The method of claim 26 or 27, where amplifying the polynucleotide sample comprises using dUTP in place of TTP.

35. The method of claim 26 or 27, where the amplification step is performed in two stages.

36. The method of claim 26 or 27, where analyzing the amplicons is performed using a method selected from the group consisting of dideoxy sequencing, pyrosequencing and SSCP.

37. A kit for screening a polynucleotide sample to detect and identity the presence of one or more than one variant in the CYP2D6 gene in the sample, comprising suitable amounts of a primer set according to claim 2.

38. The kit of claim 37, further comprising one or more than one additional reagent or one or more than one vessel to amplify the polynucleotide sample, to analyze the amplicons, or both to amplify the polynucleotide sample and to analyze the amplicons.

39. The kit of claim 38, where the additional reagent is selected from the group consisting of one or more than one DNA dependent polymerase, one or more than one buffer, one or more than one detergent and one or more than one stabilizing agent.

40. A method of screening a polynucleotide sample to detect and identify the presence of one or more than one variant in the CYP2D6 gene in the sample, comprising:
    a) providing a polynucleotide sample potentially comprising a sequence comprising at least about 50 consecutive nucleotides from one or more than one of the sequences of the wild type CYP2D6*1, SEQ ID NO:1, one or more than one variant of wild type CYP2D6*1, SEQ ID NO:1 or both wild type CYP2D6*1, SEQ ID NO:1 and one or more than one variant of wild type CYP2D6*1, SEQ ID NO:1;
    b) providing a primer set according to claim 3;
    c) amplifying the polynucleotide sample using the provided primer set to produce a set of amplicons; and
    d) analyzing the amplicons to identify the presence of CYP2D6*1 gene, SEQ ID NO: 1, the presence of one or more than one variant of the CYP2D6*1 gene, SEQ ID NO:1 or to identify one or more than one specific variant of the CYP2D6*1 gene, SEQ ID NO:1 in the sample.

41. A method of screening a population to detect and identify the presence of one or more than one variant in the CYP2D6 gene, comprising:
    a) providing a plurality of polynucleotide samples from the population;
    b) providing a primer set according to claim 3;
    c) amplifying the polynucleotide sample using the provided primer set to produce a set of amplicons; and
    d) analyzing the amplicons to detect and identify one or more than one variant of the CYP2D6*1 gene, SEQ ID NO:1 in the sample.

42. The method of claim 41, where the plurality of polynucleotide samples is a plurality of random samples of individuals in the population.

43. The method of claim 41, where the plurality of polynucleotide samples is one or more than one sample from each individual in the population.

44. The method of claim 41, where the method of screening a population further comprises determining the distribution of the variants in the CYP2D6 gene in the population.

45. The method of claim 41, where the method of screening a population further comprises recording the presence and identity, or recording the distribution of the variants in the CYP2D6 gene in the population sample, in writing or another suitable media.

46. The method of claim 40 or 41, where amplifying the polynucleotide sample comprises using modified nucleotides.

47. The method of claim 40 or 41, where the modified nucleotides are selected from the group consisting of deaza dATP, deaza dGTP, and nucleotides labeled with one or more than one label selected from the group consisting of biotin, digoxigenin, and a fluorescent dye.

48. The method of claim 40 or 41, where amplifying the polynucleotide sample comprises using dUTP in place of TTP.

49. The method of claim 40 or 41, where the amplification step is performed in two stages.

50. The method of claim 40 or 41, where analyzing the amplicons is performed using a method selected from the group consisting of dideoxy sequencing, pyrosequencing and SSCP.

51. A kit for screening a polynucleotide sample to detect and identify the presence of one or more than one variant in the CYP2D6 gene in the sample, comprising suitable amounts of a primer set according to claim 3.

52. The kit of claim 51, further comprising one or more than one additional reagent or one or more than one vessel to amplify the polynucleotide sample, to analyze the amplicons, or both to amplify the polynucleotide sample and to analyze the amplicons.

53. The kit of claim 52, where the additional reagent is selected from the group consisting of one or more than one DNA dependent polymerase, one or more than one buffer, one or more than one detergent and one or more than one stabilizing agent.

* * * * *

UNITED STATES PATENT AND TRADEMARK OFFICE
CERTIFICATE OF CORRECTION

| | | |
|---|---|---|
| PATENT NO. | : 7,195,877 B2 | Page 1 of 1 |
| APPLICATION NO. | : 10/712363 | |
| DATED | : March 27, 2007 | |
| INVENTOR(S) | : Elliott P. Dawson | |

It is certified that error appears in the above-identified patent and that said Letters Patent is hereby corrected as shown below:

Claim 2, column 84, lines 65-66: replace "; Primer Group III" with --; or Primer Group III--

Claim 11, column 85, line 42: replace "detect and identity" with --detect and identify--

Claim 22, column 86, line 38: replace "detect and identity" with --detect and identify--

Claim 37, column 87, lines 49-50: replace "detect and identity" with --detect and identify--

Signed and Sealed this

Twenty-second Day of May, 2007

JON W. DUDAS
*Director of the United States Patent and Trademark Office*

SEQUENCE LISTING

<160> NUMBER OF SEQ ID NOS: 32

<210> SEQ ID NO 1
<211> LENGTH: 9432
<212> TYPE: DNA
<213> ORGANISM: Homo sapiens

<400> SEQUENCE: 1

```
gaattcaaga ccagcctgga caacttggaa gaacccggtc tctacaaaaa atacaaaatt      60
agctgggatt gggtgcggtg gctcatgcct ataatcccag cactttggga gcctgaggtg     120
ggtggatcac ctgaagtcag gagttcaaga ctagcctggc caacatggtg aaaccctatc     180
tctactgaaa atacaaaaag ctagacgtgg tggcacacac ctgtaatccc agctacttag     240
gaggctgagg caggagaatt gcttgaagcc tagaggtgaa ggttgtagtg agccgagatt     300
gcatcattgc acaatggagg ggagccacca gcctgggcaa caagaggaaa tctccgtctc     360
caaaaaaaaa aaaaaaaaaa aaagaattag gctgggtggt gcctgtagtc ccagctactt     420
gggaggcagg gggtccactt gatgtcgaga ctgcagtgag ccatgatcct gccactgcac     480
tccggcctgg gcaacagagt gagaccctgt ctaaagaaaa aaaaaataaa gcaacatatc     540
```

-continued

```
ctgaacaaag gatcctccat aacgttccca ccagatttct aatcagaaac atggaggcca      600
gaaagcagtg gaggaggacg accctcaggc agcccgggag gatgttgtca caggctgggg      660
caagggcctt ccggctacca actgggagct ctgggaacag ccctgttgca aacaagaagc      720
catagcccgg ccagagccca ggaatgtggg ctgggctggg agcagcctct ggacaggagt      780
ggtcccatcc aggaaacctc cggcatggct gggaagtggg gtacttggtg ccgggtctgt      840
atgtgtgtgt gactggtgtg tgtgagagag aatgtgtgcc ctaagtgtca gtgtgagtct      900
gtgtatgtgt gaatattgtc tttgtgtggg tgattttctg cgtgtgtaat cgtgtccctg      960
caagtgtgaa caagtggaca agtgtctggg agtggacaag agatctgtgc accatcaggt     1020
gtgtgcatag cgtctgtgca tgtcaagagt gcaaggtgaa gtgaagggac caggcccatg     1080
atgccactca tcatcaggag ctctaaggcc ccaggtaagt gccagtgaca gataagggtg     1140
ctgaaggtca ctctggagtg ggcaggtggg ggtagggaaa gggcaaggcc atgttctgga     1200
ggaggggttg tgactacatt agggtgtatg agcctagctg ggaggtggat ggccgggtcc     1260
actgaaaccc tggttatccc agaaggcttt gcaggcttca ggagcttgga gtggggagag     1320
ggggtgactt ctccgaccag gcccctccac cggcctaccc tgggtaaggg cctggagcag     1380
gaagcagggg caagaacctc tggagcagcc catacccgcc ctggcctgac tctgccactg     1440
gcagcacagt caacacagca ggttcactca cagcagaggg caaaggccat catcagctcc     1500
ctttataagg gaagggtcac gcgctcggtg tgctgagagt gtcctgcctg gtcctctgtg     1560
cctggtgggg tgggggtgcc aggtgtgtcc agaggagccc atttggtagt gaggcaggta     1620
tggggctaga agcactggtg cccctggccg tgatagtggc catcttcctg ctcctggtgg     1680
acctgatgca ccggcgccaa cgctgggctg cacgctaccc accaggcccc ctgccactgc     1740
ccgggctggg caacctgctg catgtggact tccagaacac accatactgc ttcgaccagg     1800
tgagggagga ggtcctggag ggcggcagag gtgctgaggc tcccctacca gaagcaaaca     1860
tggatggtgg gtgaaaccac aggctggacc agaagccagg ctgagaaggg gaagcaggtt     1920
tgggggacgt cctggagaag ggcatttata catggcatga aggactggat tttccaaagg     1980
ccaaggaaga gtagggcaag ggcctggagg tggagctgga cttggcagtg ggcatgcaag     2040
cccattgggc aacatatgtt atggagtaca aagtcccttc tgctgacacc agaaggaaag     2100
gccttgggaa tggaagatga gttagtcctg agtgccgttt aaatcacgaa atcgaggatg     2160 aaggggtgc agtgacccgg ttcaaacctt ttgcactgtg ggtcctcggg cctcactgcc      2220
tcaccggcat ggaccatcat ctgggaatgg gatgctaact ggggcctctc ggcaattttg     2280
gtgactcttg caaggtcata cctgggtgac gcatccaaac tgagttcctc catcacagaa     2340
ggtgtgaccc ccaccccgc cccacgatca ggaggctggg tctcctcctt ccacctgctc      2400
actcctggta gccccggggg tcgtccaagg ttcaaatagg actaggacct gtagtctggg     2460
gtgatcctgc cttgacaaga ggccctgacc ctccctctgc agttgcgcg ccgcttcggg      2520 gacgtgttca gcctgcagct ggcctggacg ccggtggtcg tgctcaatgg gctggcggcc     2580
gtgcgcgagc cgctggtgac ccacggcgag gacaccgccg accgcccgcc tgtgcccatc     2640
acccagatcc tgggtttcgg gccgcgttcc caaggcaagc agcggtgggg acagagacag     2700
atttccgtgg gacccgggtg ggtgatgacc gtagtccgag ctgggcagag agggcgcggg     2760
gtcgtggaca tgaaacaggc cagcgagtgg ggacagcggg ccaagaaacc acctgcacta     2820
gggaggtgtg agcatgggga cgagggcggg gcttgtgacg agtgggcggg gccactgccg     2880
agacctggca ggagcccaat gggtgagcgt ggcgcatttc ccagctggaa tccggtgtcg     2940
```

-continued

```
aagtggggc gggggaccgca cctgtgctgt aagctcagtg tgggtggcgc ggggcccgcg    3000
gggtcttccc tgagtgcaaa ggcggtcagg gtgggcagag acgaggtggg gcaaagcctg    3060
ccccagccaa gggagcaagg tggatgcaca aagagtgggc cctgtgacca gctggacaga    3120
gccagggact gcgggagacc aggggagca tagggttgga gtgggtggtg gatggtgggg    3180
ctaatgcctt catggccacg cgcacgtgcc cgtcccaccc ccaggggtgt tcctggcgcg    3240
ctatgggccc gcgtggcgcg agcagaggcg cttctccgtg tccaccttgc gcaacttggg    3300
cctgggcaag aagtcgctgg agcagtgggt gaccgaggag gccgcctgcc tttgtgccgc    3360
cttcgccaac cactccggtg ggtgatgggc agaagggcac aaagcgggaa ctgggaaggc    3420
gggggacggg gaaggcgacc ccttacccgc atctcccacc cccaggacgc cccttcgcc    3480
ccaacggtct cttggacaaa gccgtgagca acgtgatcgc ctccctcacc tgcgggcgcc    3540
gcttcgagta cgacgaccct cgcttcctca ggctgctgga cctagctcag gagggactga    3600
aggaggagtc gggctttctg cgcgaggtgc ggagcgagag accgaggagt ctctgcaggg    3660
cgagctcccg agaggtgccg gggctggact ggggcctcgg aagagcagga tttgcataga    3720
tgggtttggg aaaggacatt ccaggagacc ccactgtaag aagggcctgg aggaggaggg    3780
gacatctcag acatggtcgt gggagaggtg tgcccgggtc aggggcacc aggagaggcc    3840
aaggactctg tacctcctat ccacgtcaga gatttcgatt ttaggtttct cctctgggca    3900
aggagagagg gtggaggctg gcacttgggg agggacttgg tgaggtcagt ggtaaggaca    3960
ggcaggccct gggtctacct ggagatggct ggggcctgag acttgtccag gtgaacgcag    4020
agcacaggag ggattgagac cccgttctgt ctggtgtagg tgctgaatgc tgtccccgtc    4080
ctcctgcata tcccagcgct ggctggcaag gtcctacgct tccaaaaggc tttcctgacc    4140
cagctggatg agctgctaac tgagcacagg atgacctggg acccagccca gccccccccga   4200
gacctgactg aggccttcct ggcagagatg gagaaggtga gagtggctgc cacggtgggg    4260
ggcaagggtg gtgggttgag cgtcccagga ggaatgaggg gaggctgggc aaaaggttgg    4320
accagtgcat caccccggcga gccgcatctg ggctgacagg tgcagaattg gaggtcattt    4380
gggggctacc ccgttctgtc ccgagtatgc tctcggccct gctcaggcca aggggaaccc    4440
tgagagcagc ttcaatgatg agaacctgcg catagtggtg gctgacctgt tctctgccgg    4500
gatggtgacc acctcgacca cgctggcctg gggcctcctg ctcatgatcc tacatccgga    4560
tgtgcagcgt gagcccatct gggaaacagt gcaggggccg aggaggaag ggtacaggcg    4620
ggggcccatg aactttgctg ggacacccgg ggctccaagc acaggcttga ccaggatcct    4680
gtaagcctga cctcctccaa cataggaggc aagaaggagt gtcagggccg acccctgg     4740
gtgctgaccc attgtgggga cgcatgtctg tccaggccgt gtccaacagg agatcgacga    4800
cgtgatagggg caggtgcggc gaccagagat gggtgaccag gctcacatgc cctacaccac    4860
tgccgtgatt catgaggtgc agcgctttgg ggacatcgtc ccctgggtg tgacccatat    4920
gacatcccgt gacatcgaag tacagggctt ccgcatccct aagtaggcc tggcgccctc    4980
ctcaccccag ctcagcacca gcacctggtg atagccccag catggctact gccaggtggg    5040
cccactctag gaaccctggc cacctagtcc tcaatgccac cacactgact gtccccactt    5100
gggtgggggg tccagagtat aggcagggct ggcctgtcca tccagagccc ccgtctagtg    5160
gggagacaaa ccaggacctg ccagaatgtt ggaggaccca acgcctgcag ggagagggggg   5220
cagtgtgggt gcctctgaga ggtgtgactg cgccctgctg tggggtcgga gagggtactg    5280
```

-continued

```
tggagcttct cgggcgcagg actagttgac agagtccagc tgtgtgccag gcagtgtgtg      5340
tcccccgtgt gttggtggc agggtccca gcatcctaga gtccagtccc cactctcacc       5400
ctgcatctcc tgcccaggga acgacactca tcaccaacct gtcatcggtg ctgaaggatg      5460
aggccgtctg ggagaagccc ttccgcttcc accccgaaca cttcctggat gcccagggcc      5520
actttgtgaa gccggaggcc ttcctgcctt tctcagcagg tgcctgtggg gagcccggct      5580
ccctgtcccc ttccgtggag tcttgcaggg gtatcaccca ggagccaggc tcactgacgc      5640
ccctcccctc cccacaggcc gccgtgcatg cctcggggag ccctggccc gcatggagct       5700 cttcctcttc ttcacctccc tgctgcagca cttcagcttc tcggtgccca ctggacagcc      5760
ccggcccagc caccatggtg tctttgcttt cctggtgagc ccatcccct atgagctttg       5820 tgctgtgccc cgctagaatg gggtacctag tccccagcct gctccctagc cagaggctct      5880
aatgtacaat aaagcaatgt ggtagttcca actcgggtcc cctgctcacg ccctcgttgg      5940
gatcatcctc ctcagggcaa ccccacccct gcctcattcc tgcttacccc accgcctggc      6000
cgcatttgag acagggtac gttgaggctg agcagatgtc agttaccctt gcccataatc       6060
ccatgtcccc cactgaccca actctgactg cccagattgg tgacaaggac tacattgtcc      6120
tggcatgtgg ggaaggggcc agaatgggct gactagaggt gtcagtcagc cctggatgtg      6180
gtggagaggg caggactcag cctggaggcc catatttcag gcctaactca gcccacccca      6240
catcagggac agcagtcctg ccagcaccat cacaacagtc acctcccttc atatatgaca      6300
ccccaaaacg gaagacaaat catggcgtca gggagctata tgccagggct acctacctcc      6360
cagggctcag tcggcaggtg ccagaacgtt ccctgggaag gccccatgga agcccaggac      6420
tgagccacca ccctcagcct cgtcacctca ccacaggact ggctacctct ctgggccctc      6480
agggatgctg ctgtacagac ccctgaccag tgacgagttc gcactcaggg ccaggctggc      6540
gctggaggag gacacttgtt tggctccaac cctaggtacc atcctcccag tagggatcag      6600
gcagggccca caggcctgcc ctagggacag gagtcaacct tggacccata aggcactggg      6660
gcgggcagag aaggaggagg tggcatgggc agctgagagc cagagaccct gaccctagtc      6720
cttgctctgc cattaccccg tgtgaccccg gcccaccct tccccaccct tccccacccc        6780
gggcttctgt ttccttctgc caacgagaag gctgcttcac ctgccccgag tcctgtcttc      6840
ctgctctgcc ttctggggct gtggcccttg ctggcctgga gccccaacca agggcaggga     6900
ctgctgtcct ccacgtctgt cctcaccgac ataatgggct gggctgggca cacaggcagt      6960
gcccaagagt ttctaatgag catatgatta cctgagtcct gggcagacct tcttagggaa      7020
cagcctggga cagagaacca cagacactct gaggagccac cctgaggcct cttttgccag      7080
aggaccctac agcctccctg gcagcagttc cgccagcatt tctgtaaatg ccctcatgcc      7140
agggtgcggc ccggctgtca gcacgagagg gacgttggtc tgtcccctgg caccgagtca      7200
gtcagaaggg tggccaggc cccttgggc ccctccagag acaatccact gtggtcacac        7260
ggctcggtgg caggaagtgc tgttcctgca gctgtgggga cagggagtgt ggatgaagcc      7320
aggctgggtt tgtctgaaga cggaggcccc gaaaggtggc agcctggcct atagcagcag      7380
caactcttgg atttattgga aagattttct tcacggttct gagtcttggg ggtgttagag      7440
gctcagaacc agtccagcca gagctctgtc atgggcacgt agaccggtc ccaggccctt       7500 tgctctttgc tgtcctcaga ggcctctgca aagtagaaac aggcagcctt gtgagtcccc      7560
tcctgggagc aaccaaccct ccctctgaga tgccccgggg ccaggtcagc tgtggtgaaa      7620
ggtagggatg cagccagctc agggagtggc ccagagttcc tgcccaccca aggaggctcc      7680
```

```
caggaaggtc aaggcacctg actcctgggc tgcttccctc ccctcccctc cccaggtcag    7740
gaaggtggga aagggctggg gtgtctgtga ccctggcagt cactgagaag cagggtggaa    7800
gcagccccct gcagcacgct gggtcagtgg tcttaccaga tggatacgca gcaacttcct    7860
tttgaacctt tttatttttcc tggcaggaag aagagggatc cagcagtgag atcaggcagg   7920
ttctgtgttg cacagacagg gaaacaggct ctgtccacac aaagtcggtg gggccaggat    7980
gaggcccagt ctgttcacac atggctgctg cctctcagct ctgcacagac gtcctcgctc    8040
ccctgggatg gcagcttggc ctgctggtct tggggttgag ccagcctcca gcactgcctc    8100
cctgccctgc tgcctcccac tctgcagtgc tccatggctg ctcagttgga cccacgctgg    8160
agacgttcag tcgaagcccc gggctgtcct tacctcccag tctggggtac ctgccacctc    8220
ctgctcagca ggaatggggc taggtgcttc ctcccctggg gacttcacct gctctccctc    8280
ctgggataag acggcagcct cctccttggg ggcagcagca ttcagtcctc caggtctcct    8340
gggggtcgtg acctgcagga ggaataagag ggcagactgg gcagaaaggc cttcagagca    8400
cctcatcctc ctgttctcac actgggtgt cacagtcctg ggaagttctt ccttttcagt     8460
tgagctgtgg taaccttgtg agtttcctgg aggggcctg ccactaccct tgggactccc     8520
tgccgtgtgt ctgggtctaa ctgagctctg aaaggagaga gccccagccc tgggccttcc    8580
aggggaagcc ttacctcaga ggttggcttc ttcctactct tgactttgcg tctctgcaga    8640
gggaggtggg agggtgaca caaccctgac acccacacta tgagtgatga gtagtcctgc     8700
cccgactggc ccatcctttc caggtgcagt ccccccttact gtgtctgcca agggtgccag   8760
cacagccgcc ccactccagg ggaagaggag tgccagccct taccacctga gtgggcacag    8820
tgtagcattt attcattagc ccccacactg gcctgaccat ctccctgtg ggctgcatga     8880 caaggagaga gaacaggctg aggtgagagc tactgtcaac acctaaacct aaaaaatcta    8940
taattgggct gggcagggtg gctcacgcct gtaatcccag cactttggga ggccgagatg    9000
ggtggatcac ctgaggtcag atgttcgaga ccagcctggc caacatggtg aaaccccgtc    9060
tctactaaaa atacaaaaaa ttagctgggc gtggtggtgg gtgcctgtaa tcccagctac    9120
tcaggaggct gaggcaggag aattgcttga acctgggagg cagaggctgc agtgagccga    9180
gatcgcatca ttgcactcca gcctggtcaa caagagtgaa actgtcttaa aaaaaaaatc    9240
tataattgat atctttagaa agataaaact ttgcattcat gaaataagaa taggagggtc    9300
taaaataaaa atgttcaaac acccaccacc actaattctt gacaaaaata tagtctgggt    9360
gccttagctc atgcctgtaa tcccagcatt ttgggaggct aaggcaggag gattgtttga    9420
gcctaggaat tc                                                        9432
```

<210> SEQ ID NO 2
<211> LENGTH: 1655
<212> TYPE: RNA
<213> ORGANISM: Homo sapiens

<400> SEQUENCE: 2

```
gcugagagug uccugccugg uccucugugc cugguggggu gggggugcca ggugugucca     60
gaggagccca uuugguagug aggcagguau gggggcuagaa gcacuggugc cccuggccgu   120
gauaguggcc aucuuccugc uccuggugga ccugaugcac cggcgccaac gcugggcugc   180
acgcuaccca ccaggccccc ugccacugcc cgggcugggc aaccugcugc auguggacuu   240
ccagaacaca ccauacugcu ucgaccaguu gcggcgccgc uucggggacg uguucagccu   300
```

-continued

```
gcagcuggcc uggacgccgg uggucgugcu caaugggcug gcggccgugc gcgaggcgcu      360
ggugacccac ggcgaggaca ccgccgaccg cccgccugug cccaucaccc agauccuggg      420
uuucgggccg cguucccaag ggguguuccu ggcgcgcuau gggcccgcgu ggcgcgagca      480
gaggcgcuuc uccgugucca ccuugcgcaa cuugggccug gcaagaagu cgcuggagca      540
gugggugacc gaggaggccg ccugccuuug ugccgccuuc gccaaccacu ccggacgccc      600
cuuucgcccc aacggucucu uggacaaagc cgugagcaac gugaucgccu cccucaccug      660
cgggcgccgc uucgaguacg acgacccucg cuuccucagg cugcuggacc uagcucagga      720
gggacugaag gaggagucgg gcuuucugcg cgaggugcu aaugcugucc ccguccuccu      780
gcauauccca gcgcuggcug gcaagguccu acgcuuccaa aaggcuuucc ugacccagcu      840
ggaugagcug cuaacugagc acaggaugac cugggaccca gcccagcccc ccgagaccu      900
gacugaggcc uuccuggcag agauggagaa ggccaagggg aacccugaga gcagcuucaa      960
ugaugagaac cugcgcauag uggugcugac ccuguucucu gccgggaugg ugaccaccuc     1020
gaccacgcug gccuggggcc uccugcucau gauccuacau ccggaugugc agcgccgugu     1080
ccaacaggag aucgacgacg uaauagggca ggugcggcga ccagagaugg gugaccaggc     1140
ucacaugccc uacaccacug ccgugauuca ugaggugcag cgcuuugggg acaucgucc     1200
ccuggguaug acccauauga cauccgcuga caucgaagua cagggcuucc gcaucccuaa     1260
gggaacgaca cucaucacca accugucauc ggugcugaag gaugaggccg ucugggagaa     1320
gcccuuccgc uuccaccccg aacacuuccu ggaugcccag ggccacuuug ugaagccgga     1380
ggccuuccug ccuuucucag caggccgccg ugcaugccuc ggggagcccc uggcccgcau     1440
ggagcucuuc cucuucuuca ccucccugcu gcagcacuuc agcuucucgg ugcccacugg     1500
acagccccgg cccagccacc augugucuu ugcuuuccug gugagcccau ccccuauga     1560
gcuuugugcu gugccccgcu agaaugggu accuaguccc cagccugcuc cuagcccaga     1620
ggcucuaaug uacaauaaag caaugugguu guucc     1655
```

<210> SEQ ID NO 3
<211> LENGTH: 497
<212> TYPE: PRT
<213> ORGANISM: Homo sapiens

<400> SEQUENCE: 3

```
Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
            20                  25                  30

Tyr Pro Pro Gly Pro Leu Pro Leu Pro Gly Leu Gly Asn Leu Leu His
        35                  40                  45

Val Asp Phe Gln Asn Thr Pro Tyr Cys Phe Asp Gln Leu Arg Arg Arg
    50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
                85                  90                  95

Asp Thr Ala Asp Arg Pro Pro Val Pro Ile Thr Gln Ile Leu Gly Phe
            100                 105                 110

Gly Pro Arg Ser Gln Gly Val Phe Leu Ala Arg Tyr Gly Pro Ala Trp
        115                 120                 125

Arg Glu Gln Arg Arg Phe Ser Val Ser Thr Leu Arg Asn Leu Gly Leu
```

```
                        130                 135                 140
Gly Lys Lys Ser Leu Glu Gln Trp Val Thr Glu Ala Ala Cys Leu
145                 150                 155                 160

Cys Ala Ala Phe Ala Asn His Ser Gly Arg Pro Phe Arg Pro Asn Gly
                165                 170                 175

Leu Leu Asp Lys Ala Val Ser Asn Val Ile Ala Ser Leu Thr Cys Gly
                180                 185                 190

Arg Arg Phe Glu Tyr Asp Asp Pro Arg Phe Leu Arg Leu Leu Asp Leu
            195                 200                 205

Ala Gln Glu Gly Leu Lys Glu Ser Gly Phe Leu Arg Glu Val Leu
210                 215                 220

Asn Ala Val Pro Val Leu Leu His Ile Pro Ala Leu Ala Gly Lys Val
225                 230                 235                 240

Leu Arg Phe Gln Lys Ala Phe Leu Thr Gln Leu Asp Glu Leu Leu Thr
                245                 250                 255

Glu His Arg Met Thr Trp Asp Pro Ala Gln Pro Pro Arg Asp Leu Thr
                260                 265                 270

Glu Ala Phe Leu Ala Glu Met Glu Lys Ala Lys Gly Asn Pro Glu Ser
            275                 280                 285

Ser Phe Asn Asp Glu Asn Leu Arg Ile Val Val Ala Asp Leu Phe Ser
290                 295                 300

Ala Gly Met Val Thr Thr Ser Thr Thr Leu Ala Trp Gly Leu Leu Leu
305                 310                 315                 320

Met Ile Leu His Pro Asp Val Gln Arg Val Gln Gln Glu Ile Asp
                325                 330                 335

Asp Val Ile Gly Gln Val Arg Arg Pro Glu Met Gly Asp Gln Ala His
                340                 345                 350

Met Pro Tyr Thr Thr Ala Val Ile His Glu Val Gln Arg Phe Gly Asp
            355                 360                 365

Ile Val Pro Leu Gly Val Thr His Met Thr Ser Arg Asp Ile Glu Val
                370                 375                 380

Gln Gly Phe Arg Ile Pro Lys Gly Thr Thr Leu Ile Thr Asn Leu Ser
385                 390                 395                 400

Ser Val Leu Lys Asp Glu Ala Val Trp Glu Lys Pro Phe Arg Phe His
                405                 410                 415

Pro Glu His Phe Leu Asp Ala Gln Gly His Phe Val Lys Pro Glu Ala
                420                 425                 430

Phe Leu Pro Phe Ser Ala Gly Arg Arg Ala Cys Leu Gly Glu Pro Leu
            435                 440                 445

Ala Arg Met Glu Leu Phe Leu Phe Phe Thr Ser Leu Leu Gln His Phe
450                 455                 460

Ser Phe Ser Val Pro Thr Gly Gln Pro Arg Pro Ser His His Gly Val
465                 470                 475                 480

Phe Ala Phe Leu Val Ser Pro Ser Pro Tyr Glu Leu Cys Ala Val Pro
                485                 490                 495

Arg

<210> SEQ ID NO 4
<211> LENGTH: 17060
<212> TYPE: DNA
<213> ORGANISM: Homo sapiens

<400> SEQUENCE: 4
tcatgctgcc atatcttgaa ttacaggcct ctggctggta aggagggcac tcgggaggac    60
```

-continued

```
actgcccaca ttgcaggcat gcctgtccct gcccttcaca cccccatcat gattcatgat      120
gactgcttgg ggagggcctg acacctcaaa aggccaagag tgcatacagg taatgtataa      180
agggccacat gtaacaagca cccacccaga ccatcctgct gtccctgcac cttgattctc      240
tcacagtccc aaatagaaca gtgctgccat gtaggacagg aacattcatt cagctgaggc      300
cagtttggga gaccacaagc cagatctgca gaagtcccca gataggcatg ggtcttgctc      360
tctctgtcag ttgagtagct tcaaaacttc tgttgggcca ggtggctcat gcctctattt      420
ccaacacttt ggaggccaa ggcaggagga tcacttgaag ccaggagttc cagaccagcg       480
tgggcaacat agtgaggacc catctcaaca aaaaaattag ccgagcgtaa tgatgtgcac      540
ctgtagttcc agctactcgg gacgctaaaa taggatctct tgattgaggc acaggagttt      600
gagtgagcta tgatcacagc tctgcactcc agcctgggca acagagcaag atcttgtctc      660
taaaaaatat atatatattt ttaaattta aataaactgt tctccctgcc ttttgttccc       720
cagatccagt cttcatccag acctgaaaag acccaggctc cagctgctgg cctcctgctg      780
cccctcaggc cacctgcaca ggaaattcca ggggtgggtt ggtcccactg ccagtgccgt      840
ggcctacagt gctaggcagc ccctcagtca gctagacaaa gttctccatg aatccttccc      900
agaaagtcct gttccagcct gggacaacgt ccccatggac cctcatggca ctgctggctt      960
gtcatgtcag ctatgttacc ttcctactcc ccgtggtcat cattacgttg gggcattgac     1020
tcacagcctt accaccatgc tcccagtaca cagcccagca cccagtacaa tccatacctc     1080
caacttgggt ggagctccca tgccaggcca cctctcgccc accaccctaa tctgggtagg     1140
caactagagc gagcaggggc aaggacctct gcagcagccc atacccgccc tggcctgacc     1200
ctgcacccac tggcagcaca gtcaacacag caggttggct cacagcagaa ggcaaaggcc     1260
atcatcagct ccctttataa gggaacggtc acgcgctcgg tgtgctgaga gtgtcctgcc     1320
tggtcctctg tgcctggtgg ggtgggggtg ccaggtgtgt ccagaggagc ccagttggta     1380
gtgaggcagc catggggctg gatgcactgg tgccctggc agtgacagtg gccatcttcc      1440
tgctcctggt ggacctgatg cagcagcacc aacgctggac tgcacgctac ccgccaggcc     1500
ccctgccact gcccgggctg ggcaacttgc tgcatgtgga cttccagaac atatacacct     1560
tcaaccaggt gaggggagga ggtccgtgag gatcccccac caccagcaaa catggtggt     1620 gggtggagcc acagtctgga caagaagcca ggctgagaag gggaagcaga tttgagggac     1680
ttcctgggga gggcatttat gcatggcatg aaagatggga ttttccaaag gccaaggaag     1740
agtagggcaa gggcctggag gtggagctgg acttggcagt gggcgtgcaa gcccattggg     1800
cagcatatgt taggagcaca aagtcccctc tgctgacacc agaaggaaag gccttgggaa     1860
tggaagacga gtcagggtcc tgtgtgccgt ttaaatcagg aaatcaggct gtgcgtggtg     1920
ctcacgctat aatcccagca cttaaggaag ccaaggtggg cggatcacct gaggtcaggg     1980
gttccagatg agtctggcca acatggcaaa aaccggtctc tactaaacat acaaaaaatg     2040
agctgggcac agtggtgcac gcctgcaatc ccagctactt gggaggctga ggcaggagaa     2100
ttgcttgaac ttaggaggca gaggttgtag tgagtggaga ttgtgccatt gccttgcaac     2160
ctcggtgaca cagccagaca atgtctaaat aaacgaataa gaaatcaggc cgggcgcggt     2220
ggctcacgcc tgtaatcccg gccctttgga ggctaaggcg ggcggatcat gaggttagga     2280
gatcgagacc atcctggcta acacaatgaa acccgtctct actaaagata caaaccaatt     2340
agccaggcga ggtggtgggc acctgtagtc ccagctactt gggaggctga ggcaggagaa     2400
```

-continued

```
tggcatgaac ccatgaggca gagcttgaag tgagctgaga acacaccatt acactccagt  2460
ctgggcgaca gagcgagact ctgtctcaaa aaaaaaaaaa aaaaaaaaa aaaaaaaat    2520
caacggctgg gcgcggtggc tcacacctgt aatcccagca tcttgggaga ccaaggtggg  2580
gggatcacaa ggtcaggagt tcgagaccag cctggccaac atggtgaaac cctgcctcta  2640
ctaaaaatac aaaaattagc ggggcacggt ggtgggcacc tgtaatccca gctacatggg  2700
aggctgaggc aggtgaattg cttgaacccg ggaggtggag gttgcagtga gccaagatcg  2760
cgcattgcgt ccagcctggg tgacagagcc agacatggtc taaataaatg agtaagttag  2820
aaatcaagga tgaagggata tagtggaccc ggttcaaacc ttttgcactg tgggtcctcg  2880
ggcctcactg ctcaccggca tggaccatca tctgggaatg ggatgctaac tggggcctct  2940
cggcaatttt ggtgactctt gcaaggtcat acctgggtga cgcatccaaa ctgagttcct  3000
ccatcacaga aggtgtgacc ccatccccgc cccaggatcg ggaggctggg tctcctcctt  3060
ccacctgctc actcctggta gccccgaggg tcgtctaagg ttcaaatagg actaggacct  3120
gcagtctggg gggaccctgg cctgatggag gccctgaccc aacggaggcc ctgaccctcc  3180
ctctacagct gcggcaccgc tttggggacg tgttcagcct gcagctggcc tggatgccgg  3240
tggtcgtgct caatgggctg gcggccgtgc gtgaggctct ggtgacctgc ggcgaggaca  3300
ccgccgaccg cccgcctgcg cccatctacc aggtcctggg catcgggccg cgctcccaag  3360
gcaagcggcg gtgggggaca gagactgcgt ttccgtgggt cctgggtggg cggtgaccgt  3420
agcccaagct gggctgagag ggcgtggggt tgtggacttg ggacacatag aaaggccagt  3480
gagtgggttg gggacagcga gccaggaaac cacttccact ggggaggtgc gagtctgtgg  3540
gcggaggaa gaggggcttg tgagtgggcg gggcaactgc cgagacccac caggaaccgg  3600
gtgggcggac tggcgccttt cccagctgga agcgggtgtc tagaagccgg gatggactct  3660
gctgtgggct catatgggcg gggcgggacg ggcgggatct tccctgagtg gaaaggcagt  3720
cagggtcgga agagccaagg tggggccaag acccaagcaa ggtgagtgag caaagagcag  3780
gccctgtgcc cagctggaca gggccaggga ctgcgggaga ccaggaaaag cacagggttg  3840
gagtgggcgg cggagggcgg ggccaaggcc tccatgacca cgtccatgtg tccgtcccgc  3900
ccccaggggt gtttctggca cactacggac acgcgtggcg cgagcagagg cgcttctccg  3960
tgtccacctt gcgcaacttg ggcctgggca agaagtccct ggagcggtgg gtgaccgagg  4020
aggccgcctg cctctgtgcc gccttcgccg accaagccag tgggtgatgg gcagaggggc  4080
acaaagcggg aactgggaag gtggaggact gggaaggcga cccctgaccc gcatctcccg  4140
cccccaggac gcccctttca ccccaacggc ctcctgaaca aagcggcgag caacgtgatc  4200
gcctccctca cctgcgggtg ccgcttcgag tacgacgacc ctcgcttcct caggctactg  4260
gacctagctc agaagggatt gaaggaggag ctgggctttc tgtgagagat gtggagcgag  4320
ggaccgcagg gtctctgcag ggcgagctcc tgagaggtgc cggactgca gccggacctc  4380
caaggagcag ggtttgcata gagtggtttg ggaaggaca ttccagaaga gctcactgct  4440
agaggaaggc ccttgaggag gaggagacat ctcagatacg gtcgtgggag aggtgtgccc  4500
gggtcagggg gcaccaagaa aggccaagga ccctgtgcct cctgtccaca ttggagattt  4560
tgattttag gtttctcctc tggcagccca gggcaaggag agaggtgga ggctggcact  4620
tggggaggga cttggggagg tgagtggtgg ggacaggcag gccctgggtc ttccctggag  4680
gcagctgggg cctgagactg gtccaggtga acgcagagca caggagggat tgagaccccg  4740
ttctgtgtca gctgtagatg ctgaatgttg tcccctcct cctgcgcatc ccagggctgg  4800
```

```
ctggcaaggt cctacgctcc caaaaggctt tcctgaccca gctggatgag ctgctgaccg    4860
agcacagaat gatctgggac ccagcctagc caccccgaga cctgactgag gccttcctgg    4920
cagagaagga gaaggtgaga gtggctgaca cggtagggac caggggtggt gggttgagcg    4980
tccgggagga atgaggcagg caaaaggtgg gtccattgga tcacttggca agtggcacct    5040
gggctgacag gtgcagaatg tggaggtcat ttgggggctt tcccgttctg tcccctgagt    5100
accctctcag ccctgctcag gccaagggga accctgagag cagcttcaat gatgagaacc    5160
tgcgcatggt ggtggctgac ctgttctttg ccgggatggt gaccacctcg atcacgctgg    5220
cctggggcct cctgctcatg atcctacgcc ggatgtgca gcgtgagccc agctggggcc    5280
cagtgcaggg ggcaagggag gaagggtaca gtgggggcc cctgagctta gctgggacac    5340
ccgggactcc aagcacaggc ttggccaggt tcctgtaagc ctaacctcct ccaacacagg    5400
aggcaggaga gtgtcaggc tggtcccctg ggtgctgacc cattgtgggg acgcgtgtct    5460
gtccaggccg tgtccaacag atcgacaacg tgatagggca ggtgtggtga ccagagatgg    5520
gtgaccaggc tcgcatgccc tgcaccactg ccgtgattca cgaggtgcag cgctttgggg    5580
acatcgtccc cctgggtgtg acccatatga catcccgtga catcgaagta cagggcttcc    5640
gcatccctaa ggtaggcctg gcaccctcct caccccagct cagcaccagc ccctggtgat    5700
agccccagca tggccactgc caggtgggcc cagtctagga accctggcca cccagtcctc    5760
aatgccacca catcgactgt cccagcctgg gtgtggggtg cagagtatag gcagggctgg    5820
cctgtccatc cagagcccca gtctagtggg aaggcagac caggacctgc cagaatgttg    5880 gaggaccca atacctgtag ggagagggt agcgtgggcg ctcccaggag gtgtgactgc    5940
gccctgccgt ggggtcggag agggtgctct ggagcttctc gggcacagga ctagttgaca    6000
gagtccagct gtgtgccagg cagtgtgtgt ccctgtgtg cttgggggtc ccagcatcct    6060
agagtccagt ccccactctc accctgcatc tcctgcccag gggatgatgc tcttcaccaa    6120
cctgtcatcg gtgctgaagg atgaggccgt ctggaagaag cccttccgct tccaccccga    6180
acacttcctg gatgcccagg gccactttgt gaagccggag gccttcctgc ctttctcagc    6240
aggtgcctgt ggggagcccg gctcctgtcc ccttccgtgg agtcttgcag gggtatcacc    6300
cgggagccag gctcactgac gccctcccct ccccacaggc cgccgtgcat gcctcgggcc    6360 agccctggc ccgcatagag ctcttcctct tcttcacctc cctgctgcag cacttcagct    6420
tctcggtgcc caccggacag ccccggccca gccactctcg tgtcgtcggc tttctggtga    6480
cgccatcccc ctatgagctt tgtgctgtgc cccgctagag ttgctcctca gctgggaccc    6540
tgttgtacaa taaattagtc tagtggctcc cacttggttt ctgtatccag tctgggcccc    6600
tgccaaggtc ctggttgtgt tgggtcgtca gtcacctgcc tgatgtcagt gctcacccct    6660
cacccctcac ccctcacctc attcattcat tttttttttt tttttttga gatgagcct    6720 actctgtcac ccaggctgga gtgcagtggt gcaatctcag ctcactgcaa cctccgcctc    6780
cagagttcaa gcgattctcg tgcctcagct tcctgagtag ctgggattac aggcaccggg    6840
taccaccccc ggctcatttt tgtcttttta gtagtgatgg gtttcgccat gttggccagt    6900
ctggtttcaa actcctgact tcacgtgacc accagcctca gcctcccaaa gtgctgggat    6960
tacaggcgtg agccaccgag accagcctca cctcattcac tcttacctgg acgcctgact    7020
ttacttgaga tacaggcata gtgattctca gcaggaaaca gcctgccccc acgtcacgcc    7080
cagagaccca tcactggctg cctggcttgg tgacaaagtc catgcgtaag tcttggctgg    7140
```

```
ggtggatatg aataggcata tgccaagaat caacccattc cctggctagg gtgggagact    7200
gtgttgtgct cccccagacc accctcaggt tcagtgattt ctagaaggtc tcacagccct    7260
agaaaagctg ttattctccc tgttaacagt ttattacaga aagggtaca gattaaagtc     7320
agcaaagatg aaaggcacag ggaccagagt ccagaatgac caggccaagg ctgcagctct    7380
cttttctggt ggactcctac aggcagtgct taattctccc ccaacagtaa gtgaggcagc    7440
agagagccct gccagccacg gaagctcacc tgggccttgg tgtccatggt ttttgttggg    7500
agttggtcat cctaggcttg agcccccgca gcatggctga ccttggtcat cctaggcttg    7560
agcccccgca gcatggctga cctcagttac tcagtctcca gcccctcctg aagtcagatg    7620
gatacacgtg acggccccac cctcgatcac attgttggca taaactgtgt tgtacggtcc    7680
aaggccctag ctatgtacaa agacactatt tcaggcagga cattccaagg ccttagcaga    7740
tatctcccag cctcctgtca agagtcagtt tggactcttg gtccagtggc ttgcattgtg    7800
caaggaatga cttccccact ttttactaca caggccaccc ctcttggctc taacagcaaa    7860
atgatattag tttgagcatc tgtgtgtgtg tgtgtgtgtg tgtgtgtgtg tgtgtgtttt    7920
cttgagacag ggtcttgctc tgtcaccgag gctggagtgc agtgatgcca tcagggctca    7980
ctgcagcctt gacttcctgg gttcaagcaa tcctcccatc tcagcctccc tagtagctgg    8040
gactgcaggc acatgccacc atgctttgct aatttttgta ttttttgtag agacggagtt    8100
tcaccatgtt ggccaggctg ctttcgaact ccctatctca ggtcatctga ctgcctcagc    8160
ccccagagtg ctgggattac aggtgtaagc tactgtgccc agccaaattt ccttcctaat    8220
ttcttcattg aaccactggc cattccggac catattgttt aattttcacg tgtatgtata    8280
gtttccagaa ttcctcttgt tgttgatttc cacttttatt ctgttgtggt cagagaagat    8340
gcttgatatt attttaacat ttgtaatgtt ttaagacttg ccttgtgacc taacatatgg    8400
tgtatccttg agaatgatcc atgtgctgag gagaagaatg tgtattctgc agactttaga    8460
cgaagtgttc tgtaagtatc tagtaggtcc atttcttttg tagtgcagat taagtctaat    8520
gttttcttat tgggttttcca tctgggacac ccgtccaatg ctgaatgtgg ggtgttgacg    8580
tctttagctg ttattgcgtt aacgtctctc ttgggctcca ataacatttg ctttacgtgc    8640
tccagtgttg tgtgcatatg tatttacaat tgttatattc tgttgctgga tgaccttctt    8700
tgtctcctct tacagttttt ttggttgttg ttgtttgttt gttttgtttt ggagagggag    8760
tctcgctctg tcacccaggc tggagtgcag tggcgcgatc ttggctcact gcaagcttcg    8820
cctcccaggt tgacgccatt ctcctgcctc agcctcctga gtagctggga ctacaggcgc    8880
ccgccaccac gcctggctaa ttttttgtat tttagtaga cggggttt caccatgtta       8940
gccaggatag tctcaatctc ctgacctcgt gatccgcccg cctcagcctc ccaaagtgct    9000
gggattacag gcgtgagcca ccacacccgg cctcctctta cagttttgt tttaaaatct     9060
gttctgtcta agtattgcta ctcctgctct ttttgtttt ccattggcat ggagtatctt     9120
tttccatccc tttatttca gtctatgtgt atctttacag gtgaagtgtg ttcttctag      9180
acaaagagc attgagcttt gcttttcat ccattcagcc actctgtgtc tttgtattgg      9240
agagtttagt ccatttacat tcaatgttat tattgctaag cagggactta ctcctgctat    9300
tttgttattt cttttctcac tgttttgtgg tcttctcttt tttttttttt ttccttgtct    9360
tcctttaat gaaggtgatt ttctctggtg gtatgattta atttcttgct tttttttgtg    9420
tgtgtatcca ttgtgtgttt tttcttcttt tcttttgag acacagtctc acttattgtg    9480
tgcttttga tttgaggttg ccgtgaggct tggcaaatat tatcttataa ctcattattt    9540
```

```
taaacggatg acaacactga ttgcgtaaac aaacataaag caaaaggaag actaataaaa    9600
actctacact ttaagttcat cttagtgctt tttaactttt tgttgtttct ctttttttgt    9660
ttttgagata aagtcttgct ctgttgccca ggctagagtg cagtggcacg atctcagctc    9720
actgtaacct ccacttccca ggttcaaccg attctcctgc ctcagcctcc tgggtagcag    9780
gcgcccacca ccatgcccag ctaaattttt tgtatttta gtagagatgg ggtttcacca    9840
tgttggccag gcttgtctcg aactcctgcc ctcaggtgat ccacccacct cagccttaca    9900
aagtgctggg attacctgcg tgagccaccg gtccggcct ctttatgtct tactgtactg    9960
tctgtcttga aaagtactta ttatttttga ttggttcatc atttagtcta attaaaataa    10020
gagtagttta cacaccacaa ttacagtatt ataatactct gtttttctgt gtgcttacta    10080
ttaccagtga gttttgtacc tttagatgat ttcttcttgc tcattaatat cctttttttt    10140
ttcagattga aaaactccct ttagcatttc tgtgggata taggtctggt gttgatgaaa    10200
tctcgcagct tttgtttgtc tgggaaggtc tttatttctc cttcctgttg aaggatatt    10260 tttgccagat acgttattct aggctaaaag ttttttttcc ttcagcactt taaatatgtc    10320
atgccactcc cccctggcct gtaaggtttc cactggaaag gtggctgccc catgtcatgt    10380
attggagctc tactgcatgt tatttgtttc ttttctcttg ctgcttttag gatccacgtg    10440
acagctttga ggctcaccgg gagcagcctc tggacaggag aggtcccatc caggaaacct    10500
cgggcatggc tgggaagtgg ggtacttggt gccgggtctg tatgtgtgtg tgactggtgt    10560
gtgtgagaga gaatgtgtgc cctgagtgtc agtgtgagtc tgtgtatgtg tgaatattgt    10620
ctttgtgtgg gtgattttct gcatgtgtaa tcgtgtccct gcaagtgtga acaagtggac    10680
aagtgtctgg gagtggacaa gagatctgtg caccatcagg tgtgtgcata gcgtctgtgc    10740
atgtcaagag tgcaaggtga agtgaaggga ccaggcccat gatgccactc atcatcagga    10800
gctctaaggc cccaggtaag tgccagtgac agataagggt gctgaaggtc actctggagt    10860
gggcaggtgg gggtagggaa agggcaaggt catgttctgg aggagggtt gtgactacat    10920 tagggtgtat gagcctagct gggaggtgga tggccgggtc cactgagacc ctggttatcc    10980
cagaagcctg tgtgggcttg gggagcttgg agtggggaga gggggtgact tctccgacca    11040 ggccttcta ccaccctacc ctgggtaagg gcctggagca ggaagcagcg caaggacct    11100 ctgcagcagc ccataccgc cctggcctga ccctgcaccc actggcagca cagtcaacac    11160 agcaggttg ctcacagcag agggcgaagg ccatcatcag ctcccttat aagggaaggg    11220 tcacgcgctc ggtgtgctga gagtgtcctg cctggtcctc tgtgcctggt ggggtggggg    11280
tgccaggtgt gtccagagga gcccagttgg tagtgaggca gccatggggc tagaagcact    11340
ggtgcccctg gccatgatag tggccatctt cctgctcctg gtggacctga tgcaccggca    11400
ccaacgctgg gctgcacgct acccgccagg tccctgcca ctgcccggc tgggcaacct    11460 tgctgcatgt ggacttccag aacacaccat actgcttcga ccaggtgagg gaggaggtcc    11520
tggagggcgg cagaggtcct gaggatgccc caccaccagc aaacatgggt ggtgggttaa    11580
accacaggct ggatcagaag ccaggctgag aaggggaagc aggtttgggg gactcctggg    11640
gaaggacatt tatacatggc atgaaggact ggattttcca aaggccaagg aagagtaggg    11700
caagggcctg gaggtggagc tggacttggc agtgggcatg caagcccatt gggcaacata    11760
tgttatggag tacaaagtcc cttctgctga caccagaagg aaaggccttg ggaatggaag    11820
atgagttagt cctgagtgcc gtttaaatca cgaaatcgag gatgaagggg gtgcagtgac    11880
```

-continued

```
ccggttcaaa cctttttgcac tgtgggtcct cgggcctcac tgctcaccgg catggaccat    11940
catctgggaa tgggatgcta actggggcct ctcggcaatt ttggtgactc ttgcaaggtc    12000
atacctgggt gacgcatcca aactgagttc ctccatcaca gaaggtgtga cccccacccc    12060
cgccccagga tcaggaggct gggtctcctc cttccacctg ctcactcctg gtagcccgg     12120 gggtcgtcca aggttcaaat aggactagga cctgtagtct ggggggatcc tggcttgaca    12180
agaggccctg accctccctc tgcagttgcg gcgccgcttc ggggacgtgt tcagcctgca    12240
gctggcctgg acgccggtgg tcgtgctcaa tgggctggcg gccgtgcgcg aggcgatggt    12300
gacccgcggc gaggacacgg ccgaccgccc gcctgcgccc atctaccagg tcctgggctt    12360
cgggccgcgt tcccaaggca gcggcggtg ggggacagag accgcgtttc cgtgggcccc     12420
gggtggacag tgaccgtagc ccaagcagcg ccgacagggc gtgggtcct ggacgtgaaa     12480 cagagataaa ggccagcgag tgggctgagg acagtgggcc aggaaaccac ctgcacgggg    12540
gaggtgcgag tctgtgggct gggaggggc ggggctactg cccagacccg ccagaagccc     12600
ggtgggcgag gctgatgcgt cgaagtggcg gtggcggga cgcgcctatg ctgcgggctc     12660
agtgtgggcg ggacgggcgg gatcttcctt gagtggaaag gtggtcaggg tgggcagaga    12720
cgaggtgggg ccaaaccccg ccccaggcag gggagcaatg tgggtgagca aagagtgggc    12780
cctgtgccca gctggaccgg gctagggact gcggagagacc ttgtggagcg ccagggttgg   12840
agtgggtggc ggagggtggg gccaaggcct tcatggcaac gcccacgtgt ccgtcccgcc    12900
cccaggggtg ttcctggcgc gctatgggcc cgcgtggcgc gagcagaggc gcttctccgt    12960
gtccaccttg cgcaacttgg gcctgggcaa gaagtcgctg gagcagtggg tgaccgagga    13020
ggccgcctgc ctttgtgccg ccttcgccga ccaagccggt gggtgatggg cagaagggca    13080
cacagcggga actgggaagg cggggacgg agaaggcgac cccttacccg catctcccac     13140
ccccaggacc gcccttttcgc cccaacggtc tcttggacaa agccgtgagc aacgtgatcg    13200
cctccctcac ctgcgggcgc cgcttcgagt acgacgaccc tcgcttcctc aggctgctgg    13260
acctagctca ggaggggactg aaggaggagt cgggcttcct gcgcgaggtg cggagcaagg    13320
gtctttgcag ggcgagctcc tgagaggtgc cggggctgga ctggggcctc cgaagggcag    13380
gatttgcgta gatgggtttg ggaaaggaca ttccaggaga ccccactgta agaagggcct    13440
ggaggaggag gggacatctc agacatggtc gtgggagagg tgtgcccggg tcaggggca    13500 ccaggagagg ccaaggactc tgtaccccg tccacgttgg agatttcgat tttaggtctc     13560
tcctctgggc aaggagagag agggtggagg ctggcacttg ggagggact tggtgaggtc     13620 agtggtaagg acaggcaggc cctgggtctt cctggagatg gctggggcct gagactggtc    13680
cagatgaacg cagagcacag gagggattga gacccgttc tgtctggtgt aggtgctgaa     13740
tgctgtcccc gtcctcctgc acatcccagc gctggctggc aaggtcctac gcttccaaaa    13800
ggctttcctg acccagctgg atgagctgct aactgagcac aggatgacct gggacccagc    13860
ccagcccccc cgagacctga ctgaggcctt cctggcagag atggagaagg tgagagtggc    13920
tgccacggtg gggggcaagg gtggtgggtt aacgtccca ggaggaatga ggggaggctg     13980
ggcaaaaggt tggaccagtg catcacccgg cgagccgcat ctgggctgac aggtgcagaa    14040
ttggaggtca tttgggggct accccgttct atccctgag tatcctctcg gcctgctca     14100 ggccaagggg agccctgaga gcagcttcaa tgatgagaac ctgcgcatag tggtgggtaa    14160
cctgttcctt gccgggatgg tgaccacctt gaccacgctg gcctggggcc tcctgctcat    14220
gatcctacac ctggatgtgc agcgtgagcc cagctggggc ccaaggcagg gactgaggga    14280
```

-continued

```
ggaagggtac agctgggggc ccctgggctt agctgggaca cccggggctt ccagcacagg    14340
cgtggccagg ctcctgtaag cctaacttcc tccaacacag gacgaaggag agtgtcccct    14400
gggtgctgac ccattgtggg gacgcatgtc tgtccagtcc gtgtccaaca ggagatcgac    14460
gacgtgatag ggcaggtgcg gcgaccagag atgggtgacc aggctcacat gccctacacc    14520
actgccgtga ttcacgaggt gcagcgcttt gggacatca tccccctgag tgtgacccat     14580
atgacatccc atgacatcga agtacagggc ttccgcatcc ctaaggtagg cctggcgccc    14640
tcctcacccc agctcagcat cagccccggt ggtagcccca gcatggctac tgccaggtgg    14700
gcccactcta ggaaccctgg ccacctagtc ctcaatgcca ccacactgac tgtccccgct    14760
tgggtggggg gtccagagta taggcagggc tggcctgtcc atccagagcc cccgtctagt    14820
ggggaagaca aatcaggacc tgccagaatg ttggaggacc cagcgcctgc agggagaggg    14880
ggcagtgtgg gtgcctctga gaggtgtgac tgcgccctgc tgtggggtcg agagggtac    14940
tgtggagctt ctcgggcgca ggactagttg acagagtcca gctgtgtgcc aggcagtgtg    15000
tgtcccccgt gtgtttggtg gcaggggtcc cagcatccta gagtccagtc cccactctca    15060
ccctgcatct cctgcccagg gaacgacact catcaccaac ctgtcatcgg tgctgaagga    15120
tgaggccgtc tggaagaagc ccttccgctt ccaccccgaa cacttcctgg atgcccaggg    15180
ccactttgtg aagccggagg ccttcctgcc tttctcagca ggtgcctgtg gggagcccgg    15240
ctccctgtcc ccttccgtgg agtcttgcag gggtatcacc caggagccag gctcactgac    15300
gccccctccc tccccacagg ccgccgtgca tgcctcgggg agccctggcc ccgcatggag    15360
ctcttcctct tcttcacctc cctgctgcag cacttcagct tctccgtggc cgccggacag    15420
ccccggccca gccactctcg tgtcgtcagc tttctggtga ccccatcccc ctacgagctt    15480
tgtgctgtgc cccgctagaa tggggtacct agtccccagc ctgctcccta gcagaggct    15540
ctaatgtaca ataaagcaat gtggtagttc caactcgggt cccctgctca cgccctcgtt    15600
gggatcatcc tcctcagggc aaccccaccc ctgcctcatt cctgcttacc ccaccgcctg    15660
gccgcatttg agacgggtac gttgaggctg agcagatgtc agttaccctt gcccataatc    15720
ccatgtcccc cactgaccca actctgactg cccagattgg tgacaaggac tacattgtcc    15780
tggcatgtgg ggaaggggcc agaatgggct gactagaggt gtcagtcagc cctggatgtg    15840
gtggagaggg caggactcag cctggaggcc catatttcag gcctaactca gcccacccca    15900
catcagggac agcagtcctg ccagcaccat cacaacagtc acctcccttc atatatgaca    15960
ccccaaaatg gaagacaaat catgtcaggg agctatatgc cagggctacc tcccagggct    16020
cagtcggcag gtgccagaac attccctggg aaggccccag gaaaacccag gaccgagcca    16080
ccgccctcag cctgtcacct tgtgtccaaa attggtgggt tcttggtctc actgacttca    16140
agaatgaagc cgtggaccct cacggtgagt gttacagttc ttaaagatgg tgtgttcaga    16200
gtttgttcct tctgatgtta agacgtgttc agagtttctt ccttctggtg ggtgcgtggt    16260
cttgctggct tcaggagtga agctgcagac cttcacagtg agtgttacgg ctcttaaggc    16320
tgcacgtacg gagttgttca ttcttcctgg tgggtttgtg gtctcactgg cctcaggagt    16380
gaaactgcag tccttccagt gttacaactc ataaaggcag tgtggaccca atgagggagc    16440
agcagcagca agacttactg caaacagcaa aagaatgatg gcaaccaggt tgccgctgct    16500
acttcaggca gcctgctttt attcccttat ctgaccccca cccacatcct gctgattggc    16560
ccattttaca gacagtggat tggtccactt acagagagct gattggtgca tttacaatcc    16620
```

```
ctgagctaga cacagagtac tgattggtat atttacaaac cttgagctag acacagagtg      16680
ctgaatggtg tatttacaat cccttagcta gacataaagg ttgtcccagt ccccactaga      16740
ttagctagat agagtagaca gagagcactg attggtgcgt ttacaaacct tgagttagac      16800
acagggtgct gactggtgtg tttacaaacc ttgagctaga cacagagtgc tgattggtgt      16860
atttacaatc ttttagctag aaataaaagt tccccaagtc cccaccagat tagctagata      16920
cagagtgcta attggtgcat gcacaacccg gagctagaca cagagtgctg attggtgcat      16980
atacaatcct ctggctagac ataaaagttc tccaagtccc cacctgactc agagcccagc      17040
cagcttcgcc tagtggatcc                                                   17060

<210> SEQ ID NO 5
<211> LENGTH: 13278
<212> TYPE: DNA
<213> ORGANISM: Homo sapiens

<400> SEQUENCE: 5
attaccagtg agttttgtac ctttagatga tttcttcttg ctcattaata tccttttttt        60
tttcagattg aaaaactccc tttagcattt cttgtgggat ataggtctgg tgttgatgaa       120
atctcgcagc ttttgtttgt ctgggaaggt ctttatttct ccttcctgtt ggaaggatat       180
ttttgccaga tacgttattc tcggctaaaa gttttttttc cttcagcact ttaaatatgt       240
catgccactc cccctggcc tgtaaggttt ccactggaaa ggtggctgcc ccatgtcatg        300
tattggagct ctactgcatg ttatttgttt cttttctctt gctgcttta ggatccacgt        360 gacagctttg aggctcactg ggagcagcct ctggacagga gaggtcccat ccaggaaacc      420
ttgggcatgg ctgggaagtg gggtacttgg tgccgggtct gtatgtgtgt gtgactggtg       480
tgtgtgagag agaatgtgtg ccctgagtgt cagtgtgagt ctgtgtatgt gtgaatattg       540
tctttgtgtg ggtgattttc tgcatgtgta atcgtgtccc tgcaagtgtg aacaagtgga       600
caagtgtctg ggagtggaca agagatctgt gcaccatcag gtgtgtgcat agcgtctgtg       660
catgtcaaga gtgcaaggtg aagtgaaggg accaggccca tgatgccact catcatcagg       720
agctctaagg ccccaggtaa gtgccagtga cagataaggg tgctgaaggt cactctggag       780
tgggcaggtg ggggtaggga aagggcaagg ccatgttctg gaggagggt tgtgactaca        840 ttacggtgta tgagcctagc tgggaggtgg atggccgggt ccactgagac cctggttatc       900
ccagaagcct gtgtgggctt ggggagcttg gagtggggag aggggtgac ttctccgacc       960 aggcctttct accaccctac cctgggtaag ggcctggagc aggaagcagc ggcaaggacc      1020
tctggagcag cccataccca ccctggcctg actctgccac tggcagcaca gtcaacacag      1080
caggttcact cacagcagag ggcaaaggcc atcatcagct ccctttataa gggaagggtc      1140
acgcgctcgg tgtgctgaga gtgtcctgcc tggtcctctg tgcctggtgg ggtggggtg       1200 ccaggtgtgt ccagaggagc ccagttggta gtgaggcagc catggggcta gaagcactgg      1260
tgcccctggc catgatagtg gccatcttcc tgctcctggt ggacctgatg caccggcacc      1320
aacgctgggc tgcacgctac ccgccaggtc cctgccact gccgggctg ggcaaccttg        1380 ctgcatgtgg acttccagaa cacaccatac tgcttcgacc aggtgaggga ggaggtcctg      1440
gagggcggca gaggtcctga ggatgcccca ccaccagcaa acatgggtgg tgggttaaac      1500
cacaggctgg atcagaagcc aggctgagaa ggggaagcag gtttggggga cgtcctgggg      1560
aaggacattt atacatggca tgaaggactg gattttccaa aggccaagga agagtagggc      1620
aagggcctgg aggtggagct ggacttggca gtgggcatgc aagcccattg gcaacatat       1680
```

```
gttatggagt acaaagtccc ttctgctgac accagaagga aaggccttgg gaatggaaga   1740
tgagttagtc ctgagtgccg tttaaatcac gaaatcgagg atgaaggggg tgcagtgacc   1800
cggttcaaac cttttgcact gtgggtcctc gggcctcact gctcaccggc atggaccatc   1860
atctgggaat gggatgctaa ctggggcctc tcggcaattt tggtgactct tgcaaggtca   1920
tacctggggtg acgcatccaa actgagttcc tccatcacag aaggtgtgac ccccaccccc   1980
gccccaggat caggaggctg ggtctcctcc ttccacctgc tcactcctgg tagccccggg   2040
ggtcgtccaa ggttcaaata ggactaggac ctgtagtctg gggggatcct ggcttgacaa   2100
gaggccctga ccctccctct gcagttgcgg cgccgcttcg ggacgtgtt cagcctgcag    2160
ctggcctgga cgccggtggt cgtgctcaat gggctggcgg ccgtgcgcga ggcgatggtg   2220
acccgcggcg aggacacggc cgaccgcccg cctgcgccca tctaccaggt cctgggcttc   2280
gggccgcgtt cccaaggcaa gcggcggtgg ggacagaga ccgcgtttcc gtgggccccg    2340
ggtggacagt gaccgtagcc caagcagcgc cgacagggcg tggggtcctg gacgtgaaac   2400
agagataaag gccagcgagt gggctgagga cagtgggcca ggaaaccacc tgcacggggg   2460
aggtgcgagt ctgtgggctg ggaggggggcg ggctactgcc cagacccgcc agaagcccgg  2520
tgggcgaggc tgatcgtcg aagtggcggt ggcggggacg cgcctatgct gcggctcag    2580
tgtgggcggg acggcggga tcttccttga gtggaaaggt ggtcagggtg ggcagagacg    2640
aggtgggggcc aaaccccgcc ccaggcaggg agcaatgtg ggtgagcaaa gagtgggccc   2700
tgtgcccagc tggaccgggc tagggactgc gggagacctt gtggacgcc agggttggag    2760
tgggtggcgg agggtgggcc aaggccttca tggcaacgcc cacgtgtccg tcccgcccac   2820
agggggtgatc ctgtcgcgct atgggcccgc gtggcgcgag cagaggcgct tctccgtgtc   2880
caccttgcgc aacttgggcc tgggcaagaa gtcgctggag cagtgggtga ccgaggaggc   2940
cgcctgcctt tgtgccgcct tcgccgacca agccggtggg tgatgggcag aagggcacac   3000
agcgggaact gggaaggcgg gggacggaga aggcgacccc ttacccgcat ctcccacccc   3060
caggacgccc ctttcgcccc aacggtctct tggacaaagc cgtgagcaac gtgatcgcct   3120
ccctcacctg cgggcgccgc ttcgagtacg acgaccctcg cttcctcagg ctgctggacc   3180
tagctcaggg agggatcgaa ggaggagtcg ggcttcctgc gcgaggtgcg gagcaagggt   3240
cttttgcaggg cgagctcctg agaggtgccg gggctggact ggggcctccg aagggcagga   3300
tttgcgtaga tgggtttggg aaaggacatt ccaggagacc ccactgtaag aagggcctgg   3360
aggaggaggg gacatctcag acatggtcgt gggagaggtg tgcccgggtc aggggcacc    3420
aggagaggcc aaggactctg taccccgtc cacgttggag atttcgatt taggtttctc    3480
ctctgggcaa ggagagagag ggtggaggct ggcacttggg gagggacttg gtgaggtcag   3540
tggtaaggac aggcaggccc tgggtcttcc tggagatggc tggggcctga gactggtcca   3600
gatgaacgca gagcacagga aggattgaga cccggttctg tctggtgtag gtgctgaatg   3660
ctgtccccgt cctcccgcac atcccagcgc tggctggcaa ggtcctacgc ttccaaaagg   3720
cttttcctgac ccagctggat gagctgctaa ctgagcacag gatgacctgg gacccagccc   3780
agccaccccg agacctgact gaggccttcc tggcaaagaa ggagaaggtg agagtggctg   3840
ccacggtggg gggcaagggt ggtgggttga acgtcccagg aggaatgagg ggaggctggg   3900
caaaaggttg gaccagtgca tcacccggcg agccgcatct gggctgacag gtgcagaatt   3960
ggaggtcatt tgggggctac cccgttctat cccctgagta tcctctcggc cctgctcagg   4020
```

-continued

```
ccaagggag  ccctgagagc  agcttcaatg  atgagaacct  gcgcatagtg  gtgggtaacc    4080
tgttccttgc  cgggatggtg  accaccttga  ccacgctggc  ctggggcctc  ctgctcatga    4140
tcctacacct  ggatgtgcag  cgtgagccca  gctgggggccc  aaggcaggga  ctgagggagg    4200
aagggtacag  ctgggggccc  ctgggcttag  ctgggacacc  cggggcttcc  agcacaggcg    4260
tggccaggct  cctgtaagcc  taacttcctc  caacacagga  ggaaggagag  tgtcccctgg    4320
gtgctgaccc  attgtgggga  cgcatgtctg  tccagtccgt  gtccaacagg  agatcgacga    4380
cgtgataggg  caggtgcggc  gaccagagat  gggtgaccag  gctcacatgc  cctacaccac    4440
tgccgtgatt  catgaggtgc  agcactttgg  ggactcgtcc  ccctgggtgt  gacccatatg    4500
acatcccgtg  acatcgaagt  acagggcttc  cgcatcccta  aggtaggcct  ggcgccctcc    4560
tcaccccagc  tcagcaccag  ccctggtga   tagcccagc   atggctactg  ccaggtgggc    4620
ccactctagg  aaccctggcc  acctagtcct  caatgccacc  acactgactg  tccccacttg    4680 ggtgggggt   ccagagtata  ggcagggctg  gcctgtccat  ccagagcccc  cgtctagtgg    4740
ggaagacaaa  ccaggacctg  ccagaatgtt  ggaggaccca  gcgcctgcag  ggagagggg     4800 cagtgtgggt  gcctctgaga  ggtgtgactg  cgccctgctg  tggggtcgga  gagggtactg    4860
tggagcttct  cgggcgcagg  actagttgac  agagtccagc  tgtgtgccag  gcagtgtgtg    4920 tccccgtgt   gtttggtggc  agggggtccca  gcatcctaga  gtccagtccc  cactctcacc    4980
ctgcatctcc  tgcccaggga  acgacactca  tcaccaacct  gtcatcggtg  ctgaaggatg    5040
aggccgtctg  gaagaagccc  ttccgcttcc  accccgaaca  cttcctggat  gcccagggcc    5100 acttgtgaa   gccggaggcc  ttcctgcctt  tctcagcagg  tgcctgtggg  gagcccggct    5160
ccctgtcccc  ttccgtggag  tcttgcaggg  gtatcaccca  ggagccaggc  tcactgacgc    5220
ccctcccctc  cccacaggcc  gccgtgcatg  cctcggggag  cccctggccc  gcatggagct    5280
cttcctcttc  ttcacctccc  tgctgcagca  cttcagcttc  tccgtggccg  ccggacagcc    5340
ccggcccagc  cactctcgtg  tcgtcagctt  tctggtgacc  ccatcccct   atgagctttg    5400 tgctgtgccc  cgctagaatg  gggtacctag  tccccagcct  gttccctagc  cagaggctct    5460
aatgtacaat  aaagcaatgt  ggtagttcca  actcgggtcc  cctgctcacg  ccctcgttgg    5520
gatcatcctc  ctcagggcaa  ccccacccct  gcctcattcc  tgcttacccc  accgcctggc    5580
cgcatttgag  acgggtacgt  tgaggctgag  cagatgtcag  ttacccttgc  ccataatccc    5640
gtgtccccca  ctgacccaac  tctgactgcc  cagattggtg  acaaggacta  cattgtcctg    5700
gcatgtgggg  aaggggccag  aatgggctga  ctagaggtgt  cagtcagccc  tggatgtggt    5760
ggagagggca  ggactcagcc  tggaggccca  tatttcaggc  ctaactcagc  ccaccccaca    5820
tcagggacag  cagtcctgcc  agcaccatca  caacagtcac  ctcccttcat  atatgacacc    5880
ccaaaatgga  agacaaatca  tgtcagggag  ctatatgcca  gggctacctc  ccagggctca    5940
gtcggcaggt  gccagaacat  tccctgggaa  ggccccagga  aaacccagga  ccgagccacc    6000
gccctcagcc  tgtcaccttg  tgtccaaaat  tggtgggttc  ttggtctcac  tgacttcaag    6060
aatgaagctg  tggaccctca  cggtgagtgt  tacagttctt  aaagatggtg  tgttcagagt    6120
ttgttccttc  tgatgttaag  acgtgttcag  agtttcttcc  ttctggtggg  tgcgtggtct    6180
tgctggcttc  aggagtgaag  ctgcagacct  tcacagtgag  tgttacggct  cttaaggctg    6240
cacgtacgga  gttgttcatt  cttcctggtg  ggtttgtggt  ctcactggcc  tcaggagtga    6300
aactgcagtc  cttccagtgt  tacaactcat  aaaggcagtg  tggacccaat  gagggagcag    6360
cagcagcaag  acttactgca  aacagcaaaa  gaatgatggc  aaccaggttg  ccgctgctac    6420
```

-continued

```
ttcaggcagc ctgcttttat tcccttatct gaccccacc cacatcctgc tgattggccc    6480
attttacaga cagtggattg gtccacttac agagagctga ttggtgcatt tacaatccct    6540
gagctagaca cagagtactg attggtatat ttacaaacct tgagctagac acagagtgct    6600
gaatggtgta tttacaatcc cttagctaga cataaaggtt gtcccagtcc ccactagatt    6660
agctagatag agtagacaga gagcactgat tggtgcgttt acaaaccttg agttagacac    6720
agggtgctga ctggtgtgtt tacaaaccct gagctagaca cagagtgctg attggtgtat    6780
ttacaatctt ttagctagaa ataaaggttc cccaagtccc caccagatta gctagataca    6840
gagtgctaat tggtgcatgc acgaacccgg agctagacac agagtgctga ttggtgcata    6900
tacaatcctc tggctagaca taaagttct ccaagtcccc acctgactca ggagcccagc    6960
cagcttcgcc tagtggatcc tatgccaggg ccacaggcag agctgcctgc tagtcccaca    7020
ccaggcacct gtactcctca gcccttgggc agtggacggg accaggtgcc gtggagcagt    7080
gggaggcacc catccgggag gcttgggcct cgcagggagc ccaccgtagg gaggcttggg    7140
catggcaggc tgcaagtcct gagccctgcc ccgcggggag gtgactgagg cctggcgaca    7200
attcaagtgt ggtgagcgcc ggcagcagca gtactggggg accggtgcc ccctctgcag    7260 ctgctggccc aggtgctaag cccctcactg cctggggcca gaggcaccag ccggccgctc    7320
cgagtgcagg gcccgctgag cccctgccca cccagaactg tgctggccc gcgagcaacc    7380 caggttcccg cacacgcctc tccctccata cctccccgca agcagacgga gccggctcca    7440
gcctccacca gtccagagag gggctcccac agtgcagcgc tgggctgaag ggctcctcaa    7500
gtgtggtcag agcagaagct gaggccgagg aggcgctgag agcgagcgag gaccgccagc    7560
acgttgacac ctctcaacct caccacagga ctggccacct ctctgggccc tcagggatgc    7620
tgctgtctgg acccctgacc agtgacgagt tcgcactcag ggccaggctg gcgctggagg    7680
aggacacttg tttggctcca accctaggta ccatcctccc agtagggatc aggcagggcc    7740
cacaggctgc cctagggaca ggagtcaacc ttggacccat aaggcactgg ggcgggcaga    7800
gaaggaggag gtggcatggg cagctgagag ccagagaccc tgaccctagt ccttgctctg    7860
ccattacccc gtgtgacccc gggcccaccc ttccccaccc ttccccaccc cgggcttctg    7920
tttcccttct gccaacgaga aggctgcttc acctgccccg agtcctgtct tcctgctctg    7980
ccttctgggg ctgtggccct tgctggcctg gagccccaac caagggcagg gactgctgtc    8040
ctccacatct gtcctcaccg acataatggg ctgggctggg cacacaggca gtgcccaaga    8100
gtttctaatg agcatatgat tacctgagtc ctgggcagac cttcttaggg aacagcctgg    8160
gacagagaac cacagacact ctgaggagcc acctgaggcc tcttttgcca gaggaccccta   8220 cagcctccct ggcagcagtt ccgccagcat ttctgtaaat gccctcatgc cagggtgcgg    8280
cccggctgtc agcacgagag ggacgttggt ctgtccctg gcaccgagtc agtcagaagg    8340
gtggccaggg cccccttggg cccctccaga gacaatccac tgtggtcaca cggctcggtg    8400
gcaggaagtg ctgttcctgc agctgtgggg acagggagtg tggatgaagc caggctgggt    8460
ttgtctgaag acggaggccc cgaaaggtgg cagcctggcc tatagcagca gcaactcttg    8520
gatttattgg aaagattttc ttcacggttc tgagtcttgg gggtgttaga ggctcagaac    8580
cagtccagcc agagctctgt catgggcacg tagacccggt cccagggcct tgctctttg    8640 ctgtcctcag aggcctctgc aaagtagaaa caggcagcct tgtgagtccc ctcctgggag    8700
caaccaaccc tccctctgag atgccccggg gccaggtcag ctgtggtgaa aggtagggat    8760
```

```
gcagccagct caggggagtg gcccagagtt cctgcccacc caaggaggct cccaggaagg    8820
tcaaggcacc tgactcctgg gctgcttccc tccccctccc tccccaggtc aggaaggtgg    8880
gaaagggctg gggtgtctgt gaccctggca gtcactgaga agcagggtgg aagcagcccc    8940
ctgcagcacg ctgggtcaat ggtcttacca gatggatacg cagcaacttc cttttgaacc    9000
tttttatttt cctggcagga agaagaggga tccagcagtg agatcaggca ggttctgtgt    9060
tgcacagaca gggaaacagg ctctgtccac acaaagtcgg tggggccagg atgaggccca    9120
gtctgttcac acatggctgc tgcctctcag ctctgcacag acgtcctcgc tcccctggga    9180
tggcagcttg gcctgctggt cttggggttg agccagcctc cagcactgcc tccctgccct    9240
gctgcctccc actctgcagt gctccatggc tgctcagttg acccacgct  ggagacgttc    9300 agtcgaagcc ccgggctgtc cttacctccc agtctgggt  acctgccacc tcctgctcag    9360
caggaatggg gctaggtgct tcctcccctg gggacttcac ctgctctccc tcctgggata    9420
agacggcagc ctcctccttg ggggcagcag cattcagtcc tccaggtctc ctgggggtcg    9480
tgacctgcag gaggaataag agggcagact gggcagaaag gccttcagag cacctcatcc    9540
tcctgttctc acactgggt  gtcacagtcc tgggaagttc ttccttttca gttgagctgt    9600
ggtaaccttg tgagtttcct ggaggggcct gccactaccc ttgggactcc ctgccgtgtg    9660
tctgggtcta actgagctct gaaaggagag agcccagcc  ctgggccttc caggggaagc    9720
cttacctcag aggttggctt cttcctactc ttgactttgc gtctctgcag agggaggtgg    9780 gagggtgac  acaaccctga cacccacact atgagtgatg agtagtcctg ccccgactgg    9840
cccatccttt ccaggtgcag tccccttac  tgtgtctgcc aagggtgcca gcacagccgc    9900
cccactccag gggaagagga gtgccagccc ttacccacct gagtgggcac agtgtagcat    9960
ttattcatta gcccccacac tggcctgacc atctcccctg tggctgcatg acaaggagag   10020
agaacaggct gaggtgagag ctactgtcaa cacctaaacc taaaaaatct ataattgggc   10080
tgggcagggt ggctcacgcc tgtaatccca gcactttggg aggccgagat gggtggatca   10140
cctgaggtca gatgttcgag accagcctgg ccaacatggt gaaacccgt  ctctactaaa   10200 aatacaaaaa attagctggg cgtggtggtg ggtgcctgta atcccagcta ctcaggaggc   10260
tgaggcagga gaattgcttg aacctgggag gcagaggttg cagtgagccg agatcacacc   10320
attgcactcc agtctgggtg ataagtatga aacgccatct ccaaaacaaa agaaaagcct   10380
aattccccaa gaactgtcag tctttcacct gtctgctagc tcccagggag accccacttg   10440
ccagggctgt ctacatttgt cctgagatct cttctggtgg aacagcact  ttcctcagga   10500 aagtttgttg aaagtcatca gatccatgat tgaaaatcga agctgcctgt ggtgatggat   10560
aacagctggg gttaaaaagc agcagctggg gcatgagcgg tccacagtga gttttgttg   10620 ttgttttgt  ttttttgggt gggggatggg gtcttgctag gtctcaaact cctggcctca   10680
agtcatcctc ccattacagc cttctgagtc actgacacta caggtgtgag ccaccatgtc   10740
cagcttgtag tggttttgaa cagctcttgc cccttcttgg gaatctaggt gccctgcacg   10800
tgggtaaggc tgtctgcagc tgtgcccata ttcaggaagg ccggcaaggc cctgagccct   10860
cacccgtgac tgacctgagg tgctgtgcag acagcaggtg acggctaagg gaaagttgag   10920
cactgcctag ccgagcactg aagccacgcc cggcacacag agagaccc  actcggcaaa   10980 gacttcgctt ccaggcacct aaggaactct ctgaccagtc attagctgac cactgccgta   11040
actgaagagc ggcttcagtg gccacagctc gcagggaatg gagacattaa tgcttagtca   11100
gaattagttc agaaaagtca cccagcaaag aaacagctcc aacaggcaac aacaacaaca   11160
```

```
catccttggc agggaagaga atctgacttc cggagttgcc acattatcgc ccgtgaaatg    11220
tccaggtttt aacaaattat gagacatgga aaggaaaccg aaaggacgac ccagacacgg    11280
gaaaagtcac caatgggacc agcccgatgc tgcaattgct agacaaagac gttcagtcag    11340
ctcatttaaa tatgttcaaa gacctaaaac atgctgcatc tgaggctgca ccggctggaa    11400
cctgctgatc tcggaagcta agcatggtca ggcctggcta gtacttcaaa gggagaaacc    11460
acgtgtaggc ctggtgcagt ggctcacacc tataatccta gcactctggg aagctgaggc    11520
ccgtggattg cttgagccca ggagtttgag agcagcttgg gaaatgtggt gagaccccca    11580
tctctacaaa aaatttaaaa aattagctgg ctgcctatgg tcccagcctc tcaggatgct    11640
gaggtaggag gatcacttca gcccaggaag ttgaggctgc agtgagccat gactgcatca    11700
ctgcactcca gcttgggcga cagagagacc ctctcccaag aaaagaaaa gaaccatgtc     11760 aaaagaacta acgaaagtgt gggaacaatg tctcaccaat tagagaatat caataatggg    11820
atgaacctta taaaagggg ctgggcatgg tggctcatgc ctataatccc agcactttgg      11880
gaggctgagg cgggcatatc atgaggtcaa gagattgaga ccagcctggc caacatggtg    11940
aaaccccgtc tctacttaaa atacaaaaat tagccgggcg tggtggcacg tgcctgtaat    12000
cccagctact cgggaggctg aggcaggaga atcgcttgaa cccgagaggc agagattgca    12060
gtgagccgag attgcaccac tgcactacag cctgggtgac agagcgatac tccaaaaaac    12120
aaaacaaaac aaaaaacaaa aaaaaagttt aaaaaggaac caaataaaaa ttctggagtt    12180
gtagggtaaa ataaatgaaa attcatccca ggggcccaag agcagattgg aacaattgga    12240
agaaagagcc tgtgactatg gagagaggcc acctgaggta gtcccctctg aggaacagga    12300
acaagcatga agagcaatgc acagagatcc agagacctgg agacgccgtc aagctttccg    12360
acatacacac aatgggagtc ccaggaaaga agacagggag aaaggagtaa aggaatagtt    12420
gaagaattaa tggctgaaaa acctcccaaa tctgatgaaa aatattaatc cgtacatcca    12480
aaaagctcat caaactccaa gtagggtaaa ctcaaagaga tcttcagcca tacgcatcat    12540
cataatcact gtcaaaagac agattttttct tttttttagaa ttttaaatgt accttttaat    12600
ttgctcctgg ggcaaagagc caggactggt actagagcag tgtctgggat gagaagaatt    12660
taataaaatg ggattaggtc caatggttgg gttaggggga gcaacctgct cggaaggatc    12720
agcctcaacc tatccatgca gcagggcctc cacctgtccc tctccgtagt cccacacctg    12780
gaacccagag ccatctgcct cttcccagat catggccgac agcactccac cggactgctg    12840
ctggagcagg cacaggattc acttattgag ggctgtggcc tggcacagat catagcctat    12900
acccagggac agttgtgtca cttctgccac caccacatcc gccttctgca gccacatcaa    12960
gtaccactca tggatgagcc cgtcaccccc agcggactta tcaaccccgc gtccagctcc    13020
acagccgcca cgtgctcggt gagcactggc tccaagcatg gcagctgcca tacaatccac    13080
ctgtagaggg cccggtcctc ctgtcctcag tggatgatcc cgtagaagtc cagagctcgg    13140
cagctgccct cccacaaaag acaggatttt gaaagcagca agagagaaga gacgtatcag    13200
gtagtcacag tggctcaggc ctgtaatccc agcactttgg gaggcccagg tgggaggatc    13260
gcttcacccc aggaattc                                                 13278
```

<210> SEQ ID NO 6
<211> LENGTH: 13677
<212> TYPE: DNA
<213> ORGANISM: Homo sapiens

```
<400> SEQUENCE: 6
gaattcaaga ccagcctgga caacttggaa gaacccggtc tctacaaaaa atacaaaatt      60
agctgggatt gggtgcggtg gctcatgcct ataatcccag cactttggga gcctgaggtg     120
ggtggatcac ctgaagtcag gagttcaaga ctagcctggc caacatggtg aaaccctatc     180
tctactgaaa atataaaaag ctagacgtgg tggcacacac ctgtaatccc agctacttag     240
gaggctgagg caggagaatt gcttgaagcc tagaggtgaa ggttgtagtg agccgagatt     300
gcatcattgc acaatggagg ggagccacca gcctgggcaa caagaggaaa ctccgtctc      360 caaaaaaaaa aaaaaaaaa aaaaaggatt aggctgggtg gtgcctgtag tcccagctac     420
ttgggaggca gggggtccac ttgatgtcga gactgcagtg agccatgatc ctgccactgc     480
actccggcct gggcaacaga gtgagaccct gtctaaagaa aaaaaaaata aagcaacata     540
tcctgaacaa aggatcctcc ataacgttcc caccagattt ctaatcagaa acatggaggc     600
cagaaagcag tggaggagga caaccctcag gcagcccggg aggatgttgt cacaggctgg     660
ggcaagggcc ttccggctac caactgggag ctctgggaac agccctgttg caaacaagaa     720
gccatagccc ggccagagcc caggaatgtg ggctgggctg ggagcagcct ctggacagga     780
gtggtcccat ccaggaaacc tccggcatgg ctgggaagtg gggtacttgg tgccgggtct     840
gtatgtgtgt gtgactggtg tgtgtgagag agaatgtgtg ccctaagtgt cagtgtgagt     900
ctgtgtatgt gtgaatattg tctttgtgtg ggtgattttc tgcgtgtgta atcgtgtccc     960
tgcaagtgtg aacaagtgga caagtgtctg ggagtggaca agagatctgt gcaccatcag    1020
gtgtgtgcat agcgtctgtg catgtcaaga gtgcaaggtg aagtgaaggg accaggccca    1080
tgatgccact catcatcagg agctctaagg ccccaggtaa gtgccagtga cagataaggg    1140
tgctgaaggt cactctggag tgggcaggtg ggggtaggga aagggcaagg ccatgttctg    1200
gaggaggggt tgtgactaca ttagggtgta tgagcctagc tggaggtgg atggccgggt     1260 ccactgaaac cctggttatc ccagaaggct ttgcaggctt caggagcttg gagtggggag    1320 aggggggtgac ttctccgacc aggccctcc accggcctac cctgggtaag gcctggagc    1380 aggaagcagg ggcaagaacc tctggagcag cccatacccg ccctggcctg actctgccac    1440
tggcagcaca gtcaacacag caggttcact cacagcagag ggcaaaggcc atcatcagct    1500 cccctttataa gggaagggtc acgcgctcgg tgtgctgaga gtgtcctgcc tggtcctctg    1560
tgcctggtgg ggtgggggtg ccaggtgtgt ccagaggagc ccatttggta gtgaggcagg    1620
tatgggccta gaagcactgg tgcccctggc cgtgatagtc gccatcttcc tgctcctggt    1680
ggacctgatg caccggcgcc aacgctgggc tgcacgctac tcaccaggcc ccctgccact    1740
gcccgggctg gcaacctgc tgcatgtgga cttccagaac acaccatact gcttcgacca     1800
ggtgagggag gaggtcctgg agggcggcag aggtgctgag gctcccctac cagaagcaaa    1860 catgatggt gggtgaaacc acaggctgga ccagaagcca ggctgagaag gggaagcagg    1920
tttgggggac ttcctggaga agggcattta tacatggcat gaaggactgg atttttccaaa   1980 ggccaaggaa gagtagggca agggcctgga ggtggagctg gacttggcag tgggcatgca    2040
agcccattgg gcaacatatg ttatggagta caaagtccct tctgctgaca ccagaaggaa    2100
aggccttggg aatggaagat gagttagtcc tgagtgccgt ttaaatcacg aaatcgagga    2160 tgaaggggt gcagtgaccc ggttcaaacc ttttgcactg tgggtcctcg ggcctcactg     2220
ctcaccggca tggaccatca tctgggaatg ggatgctaac tggggcctct cggcaatttt    2280
ggtgactctt gcaaggtcat acctgggtga cgcatccaaa ctgagttcct ccatcacaga    2340
```

-continued

```
aggtgtgacc cccacccccg ccccaggatc aggaggctgg gtctcctcct tccacctgct    2400
cactcctggt agccccgggg gtcgtccaag gttcaaatag gactaggacc tgtagtctgg    2460
ggggatcctg gcttgacaag aggccctgac cctccctctg cagttgcggc gccgcttcgg    2520
ggacgtgttc agcctgcagc tggcctggac gccggtggtc gtgctcaatg ggctggcggc    2580
cgtgcgcgag gcgatggtga cccgcggcga ggacacggcc gaccgcccgc ctgcgcccat    2640
ctaccaggtc ctgggcttcg ggccgcgttc ccaaggcaag cggcggtggg ggacagagac    2700
cgcgtttccg tgggccccgg gtggacagtg accgtagccc aagcagcgcc gacagggcgt    2760
ggggtcctgg acgtgaaaca gagataaagg ccagcgagtg ggctgaggac agtgggccag    2820
gaaaccacct gcacggggga ggtgcgagtc tgtgggctgg gaggggggcgg gctactgccc    2880 agacccgcca gaagcccggt gggcgaggct gatgcgtcga agtggcggtg gcggggaccg    2940
cgcctatgct gcgggctcag tgtgggcggg acgggcggga tcttccttga gtggaaaggt    3000
ggtcagggtg ggcagagacg aggtgggggcc aaaccccgcc ccaggcaggg gagcaatgtg    3060
ggtgagcaaa gagtgggccc tgtgcccagc tggaccgggc tagggactgc gggagacctt    3120
gtggagcgcc agggttggag tgggtggcgg agggtgggcc aaggccttca tggcaacgcc    3180
cacgtgtccg tcccgcccac agggggtgatc ctgtcgcgct atgggcccgc gtggcgcgag    3240
cagaggcgct tctccgtgtc caccttgcgc aacttgggcc tggcaagaa gtcgctggag    3300 cagtgggtga ccgaggaggc cgcctgcctt tgtgccgcct tcgccgacca agccggtggg    3360
tgatgggcag aagggcacac agcgggaact gggaaggcgg gggacggaga aggcgacccc    3420
ttacccgcat ctcccacccc caggacgccc ctttcgcccc aacggtctct tggacaaagc    3480
cgtgagcaac gtgatcgcct ccctcacctg cggggcgccgc ttcgagtacg acgaccctcg    3540
cttcctcagg ctgctggacc tagctcaggg agggatcgaa ggaggagtcg ggcttcctgc    3600
gcgaggtgcg gagcaagggt ctttgcaggg cgagctcctg agaggtgccg gggctggact    3660
ggggcctccg aagggcagga tttgcgtaga tgggtttggg aaaggacatt ccaggagacc    3720
ccactgtaag aagggcctgg aggaggaggg gacatctcag acatggtcgt gggagaggtg    3780
tgcccgggtc aggggggcacc aggagaggcc aaggactctg taccccgtc cacgttggag    3840 atttcgattt taggtttctc ctctgggcaa ggagagagag ggtggaggct ggcacttggg    3900
gagggacttg gtgaggtcag tggtaaggac aggcaggccc tgggtcttcc tggagatggc    3960
tggggcctga gactggtcca gatgaacgca gagcacagga aggattgaga cccggttctg    4020
tctggtgtag gtgctgaatg ctgtcccccgt cctcccgcac atcccagcgc tggctggcaa    4080
ggtcctacgc ttccaaaagg ctttcctgac ccagctggat gagctgctaa ctgagcacag    4140
gatgacctgg gacccagccc agccacccccg agacctgact gaggccttcc tggcaaagaa    4200
ggagaaggtg agagtggctg ccacggtggg gggcaagggt ggtgggttga acgtcccagg    4260
aggaatgagg ggaggctggg caaaaggttg gaccagtgca tcacccggcg agccgcatct    4320
gggctgacag gtgcagaatt ggaggtcatt tggggggctac cccgttctat ccctgagta    4380 tcctctcggc cctgctcagg ccaaggggag ccctgagagc agcttcaatg atgagaacct    4440
gcgcatagtg gtgggtaacc tgttccttgc cgggatggtg accaccttga ccacgctggc    4500
ctggggctcc tgctcatgat cctacacctg gatgtgcagc gtgagcccag ctggggccca    4560
aggcagggac tgagggagga aggtacagc tgggggcccc tgggcttagc tgggacaccc    4620
ggggcttcca gcacaggcgt ggccaggctc ctgtaagcct aacttcctcc aacacaggag    4680
```

```
gaaggagagt gtcccctggg tgctgaccca ttgtggggac gcatgtctgt ccagtccgtg   4740
tccaacagga gatcgacgac gtgatagggc aggtgcggcg accagagatg ggtgaccagg   4800
ctcacatgcc ctacaccact gccgtgattc atgaggtgca gcactttggg acatcgtcc    4860 ccctgggtgt gacccatatg acatcccgtg acatcgaagt acagggcttc cgcatccta    4920 aggtaggcct ggcgccctcc tcaccccagc tcagcaccag ccctggtga tagcccagc     4980 atggctactg ccaggtgggc ccactctagg aaccctggcc acctagtcct caatgccacc   5040
acactgactg tccccacttg ggtgggggt ccagagtata gcagggctg cctgtccat      5100 ccagagcccc cgtctagtgg ggagacaaac caggacctgc cagaatgttg gaggaccag    5160 cgcctgcagg gagaggggc agtgtgggtg cctctgagag gtgtgactgc gccctgctgt    5220
ggggtcggag agggtactgt ggagcttctc gggcgcagga ctagttgaca gagtccagct   5280
gtgtgccagg cagtgtgtgt ccccgtgtg tttggtggca ggggtcccag catcctagag    5340
tccagtcccc actctcaccc tgcatctcct gcccagggaa cgacactcat caccaacctg   5400
tcatcggtgc tgaaggatga ggccgtctgg gagaagccct tccgcttcca ccccgaacac   5460
ttcctggatg cccagggcca ctttgtgaag ccggaggcct cctgccttt ctcagcaggt    5520 gcctgtgggg agcccggctc cctgtcccct tccgtggagt cttgcagggg tatcacccag   5580
gagccaggct cactgacgcc cctccctcc ccacaggccg ccgtgcatgc ctcggggagc    5640
ccctggcccg catggagctc ttcctcttct tcacctccct gctgcagcac ttcagcttct   5700
ccgtggccgc cggacagccc cggcccagcc actctcgtgt cgtcagcttt ctggtgaccc   5760
catcccccta tgagctttgt gctgtgcccc gctagaatgg ggtacctagt ccccagcctg   5820
ttccctagcc agaggctcta atgtacaata aagcaatgtg gtagttccaa ctcgggtccc   5880
ctgctcacgc cctcgttggg atcatcctcc tcagggcaac cccacccctg cctcattcct   5940
gcttacccca ccgcctggcc gcatttgaga cgggtacgtt gaggctgagc agatgtcagt   6000 taccccttgcc cataatccag tgtcccccac tgacccaact ctgactgccc agattggtga   6060
caaggactac attgtcctgg catgtgggga aggggccaga atgggctgac tagaggtgtc   6120
agtcagccct ggatgtggtg gagagggcag gactcagcct ggaggcccat atttcaggcc   6180
taactcagcc caccccacat cagggacagc agtcctgcca gcaccatcac aacagtcacc   6240
tcccttcata tatgacaccc caaaatggaa gacaaatcat gtcagggagc tatatgccag   6300
ggctacctcc cagggctcag tcggcaggtg ccagaacatt ccctgggaag gcccaggaa    6360 aacccaggac cgagccaccg ccctcagcct gtcaccttgt gtccaaaatt ggtgggttct   6420
tggtctcact gacttcaaga atgaagctgt gacctcacgg tgagtgttac agttcttaaa   6480
gatggtgtgt tcagagtttg ttccttctga tgttaagacg tgttcagagt ttcttccttc   6540
tggtgggtgc gtggtcttgc tggcttcagg agtgaagctg cagaccttca cagtgagtgt   6600
tacggctctt aaggctgcac atacggagtt gttcattctt cctggtgggt ttgtggtctc   6660
actggcctca ggagtgaaac tgcagtcctt ccagtgttac aactcataaa ggcagtgtgg   6720
acccaatgag ggagcagcag cagcaagact tactgcaaac agcaaaagaa tgatggcaac   6780
caggttgccg ctgctacttc aggcagcctg cttttattcc cttatctgac ccccacccac   6840
atcctgctga ttggcccatt ttacagacag tggattggtc cacttacaga gagctgattg   6900
gtgcatttac aatccctgag ctagacacag agtactgatt ggtatattta caaaccttga   6960
gctagacaca gagtgctgaa tggtgtattt acaatccctt agctagacat aaaggttgtc   7020
ccagtcccca ctagattagc tagatagagt agacagagag cactgattgg tgcgtttaca   7080
```

```
aaccttgagt tagacacagg gtgctgactg gtgtgtttac aaaccctgag ctagacacag    7140
agtgctgatt ggtgtattta caatcttttta gctagaaata aaggttcccc aagtccccac   7200
cagattagct agatacagag tgctaattgg tgcatgcacg aacccggagc tagacacaga    7260
gtgctgattg gtgcatatac aatcctctgg ctagacataa aagttctcca agtccccacc   7320
tgactcagga gcccagccag cttcgcctag tggatcctat gccagggcca caggcagagc   7380
tgcctgctag tcccacacca ggcacctgta ctcctcagcc cttgggcagt ggacgggacc    7440
aggtgccgtg gagcagtggg aggcacccat ccgggaggct tgggcctcgc agggagccca   7500
ccgtagggag gcttgggcat ggcaggctgc aagtcctgag ccctgccccg cggggaggtg    7560
actgaggcct ggcgacaatt caagtgtggt gagcgccggc aggccagcag tactgggggga  7620
cccggtgccc cctctgcagc tgctggccca ggtgctaagc ccctcactgc ctggggccag   7680
aggcaccagc cggccgctcc gagtgcaggg cccgctgagc ccctgcccac ccagaactgg    7740
tgctggcccg cgagcaaccc aggttcccgc acacgcctct ccctccatac ctccccgcaa   7800
gcagacggag ccggctccag cctccaccag tccagagagg ggctcccaca gtgcagcgct    7860
gggctgaagg gctcctcaag tgtggtcaga gcagaagctg aggccgagga ggcgctgaga   7920
gcgagcgagg accgccagca cgttgacacc tctcaacctc accacaggac tggccacctc    7980
tctgggccct cagggatgct gctgtctgga cccctgacca gtgacgagtt cgcactcagg   8040
gccaggctgg cgctggagga ggacacttgt ttggctccaa ccctaggtac catcctccca    8100
gtagggatca ggcagggccc acaggcctgc cctagggaca ggagtcaacc ttggacccat   8160
aaggcactgg ggcgggcaga aaggaggag gtggcatggg cagctgagag ccagagaccc     8220
tgaccctagt ccttgctctg ccattacccc gtgtgacccc gggcccaccc ttccccaccc   8280
ttccccaccc ttccccaccc ttccccaccc cgggcttctg tttccttctg ccaacgagaa    8340
ggctgcttca cctgccccga gtcctgtctt cctgctctgc cttctgggc tgtgccctt     8400
gctggcctgg agcccaacc aagggcaggg actgctgtcc tccacatctg tcctcaccga    8460
cataatgggc tgggctgggc acacaggcag tgcccaagag tttctaatga gcatatgatt   8520
acctgagtcc tgggcagacc ttcttaggga acagcctggg acagagaacc acagacactc    8580
tgaggagcca cctgaggcct cttttgccag aggaccctac agcctccctg gcagcagttc   8640
cgccagcatt tctgtaaatg ccctcatgcc agggtgcggc ccggctgtca gcacgagagg    8700
gacgttggtc tgtcccctgg caccgagtca gtcagaaggg tggccagggc ccccttgggc   8760
ccctccagag acaatccact gtggtcacac ggctcggtgg caggaagtgc tgttcctgca    8820
gctgtgggga cagggagtgt ggatgaagcc aggctgggtt tgtctgaaga cggaggcccc   8880
gaaaggtggc agcctggcct atagcagcag caactcttgg atttattgga aagattttct    8940
tcacggttct gagtcttggg ggtgttagag gctcagaacc agtccagcca gagctctgtc   9000
atgggcacgt agacccggtc ccagggcctt tgctcttttgc tgtcctcaga ggcctctgca   9060
aagtagaaac aggcagcctt gtgagtcccc tcctgggagc aaccaaccct ccctctgaga    9120
tgccccgggg ccaggtcagc tgtggtgaaa ggtagggatg cagccagctc agggagtgg    9180
cccagagttc ctgcccaccc aaggaggctc caggaaggt caaggcacct gactcctggg     9240
ctgcttccct cccctcccct cccaggtca ggaaggtggg aaagggctgg ggtgtctgtg     9300
accctggcag tcactgagaa gcagggtgga agcagccccc tgcagcacgc tgggtcaatg   9360
gtcttaccag atggatacgc agcaacttcc ttttgaacct ttttattttc ctggcaggaa   9420
```

```
gaagagggat ccagcagtga gatcaggcag gttctgtgtt gcacagacag ggaaacaggc   9480
tctgtccaca caaagtcggt ggggccagga tgaggcccag tctgttcaca catggctgct   9540
gcctctcagc tctgcacaga cgtcctcgct cccctgggat ggcagcttgg cctgctggtc   9600
ttggggttga gccagcctcc agcactgcct ccctgccctg ctgcctccca ctctgcagtg   9660
ctccatggct gctcagttgg acccacgctg agacgttca gtcgaagccc cgggctgtcc    9720
ttacctccca gtctggggta cctgccacct cctgctcagc aggaatgggg ctaggtgctt   9780
cctcccctgg ggacttcacc tgctctccct cctgggataa gacggcagcc tcctccttgg   9840
gggcagcagc attcagtcct ccaggtctcc tgggggtcgt gacctgcagg aggaataaga   9900
gggcagactg ggcagaaagg ccttcagagc acctcatcct cctgttctca cactggggtg   9960
tcacagtcct gggaagttct tccttttcag ttgagctgtg gtaaccttgt gagtttcctg  10020
gagggggcct gccactaccc ttgggactcc ctgccgtgtg tctgggtcta actgagctct  10080
gaaaggagag agcccagcc ctgggccttc caggggaagc cttacctcag aggttggctt   10140
cttcctactc ttgactttgc gtctctgcag agggaggtgg gagggtgac acaaccctga   10200 cacccacact atgagtgatg agtagtcctg ccccgactgg cccatccttt ccaggtgcag  10260
tcccccttac tgtgtctgcc aagggtgcca gcacagccgc cccactccag gggaagagga  10320
gtgccagccc ttacccacct gagtgggcac agtgtagcat ttattcatta gcccccacac  10380
tggcctgacc atctcccctg tggctgcatg acaaggagag agaacaggct gaggtgagag  10440
ctactgtcaa cacctaaacc taaaaaatct ataattgggc tggcagggt ggctcacgcc   10500 tgtaatccca gcactttggg aggccgagat gggtggatca cctgaggtca gatgttcgag  10560
accagcctgg ccaacatggt gaaacccccgt ctctactaaa aatacaaaaa attagctggg  10620
cgtggtggtg ggtgcctgta atcccagcta ctcaggaggc tgaggcagga gaattgcttg  10680
aacctgggag gcagaggttg cagtgagccg agatcacacc attgcactcc agtctgggtg  10740
ataagtatga aacgccatct ccaaaacaaa agaaaagcct aattccccaa gaactgtcag  10800 tcttcacct gtctgctagc tcccaggggag acccccacttg ccagggctgt ctacatttgt  10860
cctgagatct cttctggtgg aacagcact ttcctcagga aagtttgttg aaagtcatca   10920
gatccatgat tgaaaatcga agctgcctgt ggtgatggat aacagctggg gttaaaaagc  10980
agcagctggg gcatgagcgg tccacagtga gttttttgttg ttgttttttgt ttttttgggt  11040 gggggatggg gtcttgctag gtctcaaact cctggcctca agtcatcctc ccattacagc  11100
cttctgagtc actgacacta caggtgtgag ccaccatgtc cagcttgtag tggttttgaa  11160
cagctcttgc cccttcttgg gaatctaggt gccctgcacg tgggtaaggc tgtctgcagc  11220
tgtgcccata ttcaggaagg ccggcaaggc ctgagccctc acccgtgact gacctgaggt  11280
gctgtgcaga cagcaggtga cggctaaggg aaagttgagc actgcctagc cgagcactga  11340
agccacgccc ggcacacaga gagacccca ctcggcaaag acttcgcttc caggcaccta   11400
aggaactctc tgaccagtca ttagctgacc actgccgtaa ctgaagagcg gcttcagtgg  11460
ccacagctcg cagggaatgg agacattaat gcttagtcag aattagttca gaaaagtcac  11520
ccagcaaaga aacagctcca acaggcaaca acaacaacac atccttggca gggaagagaa  11580
tctgacttcc ggagttgcca cattatcgcc cgtgaaatgt ccaggttttta acaaattatg  11640 agacatggaa aggaaaccga aaggacgacc cagacacggg aaaagtcacc aatgggacca  11700
gcccgatgct gcaattgcta gacaaagacg ttcagtcagc tcatttaaat atgttccaaag  11760 acctaaaaca tgctgcatct gaggctgcac cggctggaac ctgctgatct cggaagctaa  11820
```

```
gcatggtcag gcctggctag tacttcaaag ggagaaacca cgtgtaggcc tggtgcagtg    11880
gctcacacct ataatcctag cactctggga agctgaggcc cgtggattgc ttgagcccag    11940
gagtttgaga gcagcttggg aaatgtggtg agaccccat ctctacaaaa aatttaaaaa     12000
attagctggc tgcctatggt cccagcctct caggatgctg aggtaggagg atcacttcag    12060
cccaggaagt tgaggctgca gtgagccatg actgcatcac tgcactccag cttgggcgac    12120
agagagaccc tctcccaaga aaagaaaag aaccatgtca aagaactaa cgaaagtgtg      12180 ggaacaatgt ctcaccaatt agagaatatc aataatggga tgaaccttat aaaagggc      12240 tgggcatggt ggctcatgcc tataatccca gcactttggg aggctgaggc gggcatatca    12300
tgaggtcaag agattgagac cagcctggcc aacatggtga accccgtct ctacttaaaa     12360 tacaaaaatt agccgggcgt ggtggcacgt gcctgtaatc ccagctactc gggaggctga    12420
ggcaggagaa tcgcttgaac ccgagaggca gagattgcag tgagccgaga ttgcaccact    12480
gcactacagc ctgggtgaca gagcgatact ccaaaaaaca aaacaaaaca aaaacaaaa     12540 aaaaagttta aaaggaacc aaataaaaat tctggagttg tagggtaaaa taatgaaaa      12600 ttcatcccag ggcccaaga gcagattgga acaattggaa gaaagagcct gtgactatgg     12660
agagaggcca cctgaggtag tcccctctga ggaacaggaa caagcatgaa gagcaatgca    12720
cagagatcca gagacctgga gacgccgtca agctttccga catacacaca atgggagtcc    12780
caggaaagaa gacagggaga aaggagtaaa ggaatagttg aagaattaat ggctgaaaaa    12840
cctcccaaat ctgatgaaaa atattaatcc gtacatccaa aaagctcatc aaactccaag    12900
tagggtaaac tcaaagagat cttcagccat acgcatcatc ataatcactg tcaaaagaca    12960 gattttctt tttttagaat tttaaatgta ccttttaatt tgctcctggg gcaaagagcc     13020
aggactggta ctagagcagt gtctgggatg agaagaattt aataaaatgg gattaggtcc    13080
aatggttggg ttaggggagg caacctgctc ggaaggatca gcctcaacct atccatgcag    13140
cagggcctcc acctgtccct ctccgtagtc ccacacctgg aacccagagc catctgcctc    13200
ttcccagatc atggccgaca gcactccacc ggactgctgc tggagcaggc acaggattca    13260
cttattgagg gctgtggcct ggcacagatc atagcctata cccagggaca gttgtgtcac    13320
ttctgccacc accacatccg ccttctgcag ccacatcaag taccactcat ggatgagccc    13380
gtcaccccca gcggacttat caaccccgcg tccagctcca cagccgccac gtgctcggtg    13440
agcactggct ccaagcatgg cagctgccat acaatccacc tgtagagggc ccggtcctcc    13500
tgtcctcagt ggatgatccc gtagaagtcc agagctcggc agctgccctc ccacaaaaga    13560 caggatttg aaagcagcaa gagagaagag acgtatcagg tagtcacagt ggctcaggcc     13620
tgtaatccca gcactttggg aggcccaggt gggaggatcg cttaccccca ggaattc       13677
```

<210> SEQ ID NO 7
<211> LENGTH: 4375
<212> TYPE: DNA
<213> ORGANISM: Homo sapiens

<400> SEQUENCE: 7

```
cgcgctcggt gtgctgagag tgtcctgcct ggtcctctgt gcctggtggg gtggggtgc      60 caggtgtgtc cagaggagcc cagttggtag tgaggcagcc atggggctag aagcactggt    120 gccccctggcc atgatagtgg ccatcttcct gctcctggtg gacctgatgc accggcacca    180
acgctgggct gcacgctacc cgccaggtcc cctgccactg cccgggctgg gcaaccttgc    240
```

```
tgcatgtgga cttccagaac acaccatact gcttcgacca ggtgagggag gaggtcctgg      300
agggcggcag aggtcctgag gatgccccac caccagcaaa catgggtggt gggttaaacc      360
acaggctgga tcagaagcca ggctgagaag gggaagcagg tttggggac gtcctgggga      420 aggacattta tacatggcat gaaggactgg attttccaaa ggccaaggaa gagtagggca      480
agggcctgga ggtggagctg gacttggcag tgggcatgca agcccattgg gcaacatatg      540
ttatggagta caaagtccct tctgctgaca ccagaaggaa aggccttggg aatggaagat      600
gagttagtcc tgagtgccgt ttaaatcacg aaatcgagga tgaaggggt gcagtgaccc       660 ggttcaaacc ttttgcactg tgggtcctcg ggcctcactg ctcaccggca tggaccatca      720
tctgggaatg ggatgctaac tggggcctct cggcaatttt ggtgactctt gcaaggtcat      780
acctgggtga cgcatccaaa ctgagttcct ccatcacaga aggtgtgacc cccaccccg       840 ccccaggatc aggaggctgg gtctcctcct tccacctgct cactcctggt agccccgggg      900
gtcgtccaag gttcaaatag gactaggacc tgtagtctgg ggggatcctg gcttgacaag     960
aggccctgac cctccctctg cagttgcggc gccgcttcgg ggacgtgttc agcctgcagc     1020
tggcctggac gccggtggtc gtgctcaatg ggctggcggc cgtgcgcgag gcgatggtga     1080
cccgcggcga ggacacggcc gaccgcccgc ctgcgcccat ctaccaggtc ctgggcttcg     1140
ggccgcgttc ccaaggcaag cggcggtggg ggacagagac cgcgtttccg tgggccccgg     1200
gtggacagtg accgtagccc aagcagcgcc gacagggcgt gggtcctgg acgtgaaaca      1260 gagataaagg ccagcgagtg ggctgaggac agtgggccag gaaaccacct gcacggggga     1320
ggtgcgagtc tgtgggctgg gagggggcgg gctactgccc agacccgcca gaagcccggt     1380
gggcgaggct gatgcgtcga agtggcggtg gcggggacgc gcctatgctg cgggctcagt     1440
gtgggcggga cgggcgggat cttccttgag tggaaaggtg gtcagggtgg gcagagacga     1500 ggtgggggcca aaccccgccc caggcagggg agcaatgtgg gtgagcaaag agtgggccct    1560
gtgcccagct ggaccgggct agggactgcg ggagaccttg tggagcgcca gggttggagt     1620
gggtggcgga gggtgggcca aggccttcat ggcaacgccc acgtgtccgt cccgcccaca     1680
ggggtgatcc tgtcgcgcta tgggcccgcg tggcgcgagc agaggcgctt ctccgtgtcc     1740
accttgcgca acttgggcct gggcaagaag tcgctggagc agtgggtgac cgaggaggcc     1800
gcctgccttt gtgccgcctt cgccgaccaa gccggtgggt gatgggcaga agggcacaca     1860
gcgggaactg ggaaggcggg ggacggagaa ggcgacccct tacccgcatc tcccaccccc     1920
aggacgcccc tttcgcccca acggtctctt ggacaaagcc gtgagcaacg tgatcgcctc     1980
cctcacctgc gggcgccgct tcgagtacga cgaccctcgc ttcctcaggc tgctggacct     2040
agctcaggga gggatcgaag gaggagtcgg gcttcctgcg cgaggtgcgg agcaagggtc     2100
tttgcagggc gagctcctga gaggtgccgg ggctggactg gggcctccga agggcaggat     2160
ttgcgtagat gggtttggga aaggacattc caggagaccc cactgtaaga agggcctgga     2220
ggaggagggg acatctcaga catggtcgtg ggagaggtgt gcccgggtca ggggcacca      2280 ggagaggcca aggactctgt accccgtcc acgttggaga tttcgatttt aggtttctcc      2340
tctgggcaag gagagagagg gtggaggctg gcacttgggg agggacttgg tgaggtcagt     2400
ggtaaggaca ggcaggccct gggtcttcct ggagatggct ggggcctgag actggtccag     2460
atgaacgcag agcacaggaa ggattgagac ccggttctgt ctggtgtagg tgctgaatgc     2520
tgtccccgtc ctcccgcaca tcccagcgct ggctggcaag gtcctacgct tccaaaaggc     2580
tttcctgacc cagctggatg agctgctaac tgagcacagg atgacctggg acccagccca    2640
```

-continued

```
gccaccccga gacctgactg aggccttcct ggcaaagaag gagaaggtga gagtggctgc    2700
cacggtgggg ggcaagggtg gtgggttgaa cgtcccagga ggaatgaggg gaggctgggc    2760
aaaaggttgg accagtgcat cacccggcga gccgcatctg gctgacaggt gcagaattg    2820
gaggtcattt gggggctacc ccgttctatc ccctgagtat cctctcggcc ctgctcaggc    2880
caaggggagc cctgagagca gcttcaatga tgagaacctg cgcatagtgg tgggtaacct    2940
gttccttgcc gggatggtga ccaccttgac cacgctggcc tggggcctcc tgctcatgat    3000
cctacacctg gatgtgcagc gtgagcccag ctggggccca aggcagggac tgagggagga    3060
agggtacagc tgggggcccc tgggcttagc tgggacaccc ggggcttcca gcacaggcgt    3120
ggccaggctc ctgtaagcct aacttcctcc aacacaggag gaaggagagt gtccctggg    3180
tgctgaccca ttgtggggac gcatgtctgt ccagtccgtg tccaacagga gatcgacgac    3240
gtgataggc aggtgcggcg accagagatg ggtgaccagg ctcacatgcc ctacaccact    3300
gccgtgattc atgaggtgca gcactttggg gactcgtccc cctgggtgtg acccatatga    3360
catcccgtga catcgaagta cagggcttcc gcatccctaa ggtaggcctg gcgccctcct    3420
caccccagct cagcaccagc ccctggtgat agccccagca tggctactgc caggtgggcc    3480
cactctagga accctggcca cctagtcctc aatgccacca cactgactgt ccccacttgg    3540
gtgggggtc cagagtatag gcagggctgg cctgtccatc cagagccccc gtctagtggg    3600
gaagacaaac caggacctgc cagaatgttg gaggacccag cgcctgcagg gagaggggc    3660
agtgtgggtg cctctgagag gtgtgactgc gccctgctgt ggggtcggag agggtactgt    3720
ggagcttctc gggcgcagga ctagttgaca gagtccagct gtgtgccagg cagtgtgtgt    3780
cccccgtgtg tttggtggca ggggtcccag catcctagag tccagtcccc actctcaccc    3840
tgcatctcct gcccagggaa cgacactcat caccaacctg tcatcggtgc tgaaggatga    3900
ggccgtctgg aagaagccct tccgcttcca ccccgaacac ttcctggatg cccagggcca    3960
ctttgtgaag ccggaggcct tcctgccttt ctcagcaggt gcctgtgggg agcccggctc    4020
cctgtcccct tccgtggagt cttgcagggg tatcacccag gagccaggct cactgacgcc    4080
cctcccctcc ccacaggccg ccgtgcatgc ctcggggagc ccctggcccg catggagctc    4140
ttcctcttct tcacctccct gctgcagcac ttcagcttct ccgtggccgc cggacagccc    4200
cggcccagcc actctcgtgt cgtcagcttt ctggtgaccc catcccccta tgagctttgt    4260
gctgtgcccc gctagaatgg ggtacctagt ccccagcctg ttcccctagcc agaggctcta    4320
atgtacaata aagcaatgtg gtagttccaa ctcgggtccc ctgctcacgc cctcg         4375
```

<210> SEQ ID NO 8
<211> LENGTH: 5325
<212> TYPE: DNA
<213> ORGANISM: Homo sapiens

<400> SEQUENCE: 8

```
cgcgctcggt gtgctgagag tgtcctgcct ggtcctctgt gcctggtggg gtgggggtgc      60
caggtgtgtc cagaggagcc cagttggtag tgaggcagcc atggggctgg atgcactggt     120
gccctggca gtgacagtgg ccatcttcct gctcctggtg gacctgatgc agcagcacca     180
acgctggact gcacgctacc cgccaggccc cctgccactg cccgggctgg gcaacttgct     240
gcatgtggac ttccagaaca tatacacctt caaccaggtg aggggaggag gtccgtgagg     300
atccccacc accagcaaac atgggtggtg ggtggagcca cagtctggac aagaagccag     360
```

```
gctgagaagg ggaagcagat ttgagggact tcctggggag ggcatttatg catggcatga      420
aagatgggat tttccaaagg ccaaggaaga gtagggcaag ggcctggagg tggagctgga      480
cttggcagtg ggcgtgcaag cccattgggc agcatatgtt aggagcacaa agtcccctct      540
gctgacacca gaaggaaagg ccttgggaat ggaagacgag tcaggqtcct gtgtgccgtt      600 taaatcagga aatcaggctg tgcgtggtgc tcacgctata atcccagcac ttaaggaagc      660
caaggtgggc ggatcacctg aggtcagggg ttccagatga gtctggccaa catggcaaaa      720
accggtctct actaaacata caaaaaatga gctgggcaca gtggtgcacg cctgcaatcc      780
cagctacttg ggaggctgag gcaggagaat tgcttgaact taggaggcag aggttgtagt      840
gagtggagat tgtgccattg ccttgcaacc tcggtgacac agccagacaa tgtctaaata      900
aacgaataag aaatcaggcc gggcgcgtg gctcacgcct gtaatcccgg ccctttggag       960
gctaaggcgg gcggatcatg aggttaggag atcgagacca tcctggctaa cacaatgaaa     1020
cccgtctcta ctaaagatac aaaccaatta gccaggcgag tggtgggca cctgtagtcc      1080 cagctacttg ggaggctgag gcaggagaat ggcatgaacc catgaggcag agcttgaagt     1140
gagctgagaa cacaccatta cactccagtc tgggcgacag agcgagactc tgtctcaaaa     1200
aaaaaaaaaa aaaaaaaaa aaaaaaatc aacggctggg cgcggtggct cacacctgta      1260
atcccagcat cttgggagac caaggtgggg ggatcacaag gtcaggagtt cgagaccagc     1320
ctggccaaca tggtgaaacc ctgcctctac taaaaataca aaaattagcg gggcacggtg     1380
gtgggcacct gtaatcccag ctacatggga ggctgaggca ggtgaattgc ttgaacccgg     1440
gaggtggagg ttgcagtgag ccaagatcgc gcattgcgtc cagcctgggt gacagagcca     1500
gacatggtct aaataaatga gtaagttaga aatcaaggat gaagggatat agtggacccg     1560
gttcaaacct tttgcactgt gggtcctcgg gcctcactgc tcaccggcat ggaccatcat     1620
ctgggaatgg gatgctaact ggggcctctc ggcaattttg gtgactcttg caaggtcata     1680
cctgggtgac gcatccaaac tgagttcctc catcacagaa ggtgtgaccc catccccgcc     1740
ccaggatcgg gaggctgggt ctcctccttc cacctgctca ctcctggtag ccccgagggt     1800
cgtctaaggt tcaaatagga ctaggacctg cagtctgggg ggaccctggc ctgatggagg     1860
ccctgaccca acggaggccc tgaccctccc tctacagctg cggcaccgct ttggggacgt     1920
gttcagcctg cagctggcct ggatgccggt ggtcgtgctc aatgggctgg cggccgtgcg     1980
tgaggctctg gtgacctgcg gcgaggacac cgccgaccgc ccgcctgcgc ccatctacca     2040
ggtcctgggc atcgggccgc gctcccaagg caagcggcgg tggggacag agactgcgtt      2100 tccgtgggtc ctgggtgggc ggtgaccgta gcccaagctg gctgagagg gcgtggggtt     2160 gtggacttgg gacacataga aaggccagtg agtgggttgg ggacagcgag ccaggaaacc     2220
acttccactg gggaggtgcg agtctgtggg cgggaggaag aggggcttgt gagtgggcgg     2280
ggcaactgcc gagacccacc aggaaccggg tgggcggact ggcgccttc ccagctggaa      2340 gcgggtgtct agaagccggg atggactctg ctgtgggctc atatgggcgg ggcgggacgg     2400
gcgggatctt ccctgagtgg aaaggcagtc agggtcggaa gagccaaggt ggggccaaga     2460
cccaagcaag gtgagtgagc aaagagcagg ccctgtgccc agctggacag ggccagggac     2520
tgcgggagac caggaaaagc acaggggttgg agtgggcggc ggagggcggg gccaaggcct     2580
ccatgaccac gtccatgtgt ccgtcccgcc ccaggggtg tttctggcac actacggaca      2640
cgcgtggcgc gagcagaggc gcttctccgt gtccaccttg cgcaacttgg gcctgggcaa     2700
gaagtccctg gagcggtggg tgaccgagga ggccgcctgc ctctgtgccg ccttcgccga    2760
```

```
ccaagccagt gggtgatggg cagaggggca caaagcggga actgggaagg tggaggactg      2820
ggaaggcgac ccctgacccg catctcccgc ccccaggacg ccccttttcac cccaacggcc     2880 tcctgaacaa agcggcgagc aacgtgatcg cctccctcac ctgcgggtgc cgcttcgagt      2940
acgacgaccc tcgcttcctc aggctactgg acctagctca gaagggattg aaggaggagc     3000
tgggctttct gtgagagatg tggagcgagg accgcaggg tctctgcagg gcagctcct       3060 gagaggtgcc gggactgcag ccggacctcc aaggagcagg gtttgcatag agtggtttgg     3120
gaaaggacat tccagaagag ctcactgcta gaggaagggc cttgaggagg aggagacatc     3180
tcagatacgg tcgtgggaga ggtgtgcccg ggtcagggggg caccaagaaa ggccaaggac    3240
cctgtgcctc ctgtccacat tggagatttt gatttttagg tttctcctct ggcagcccag    3300
ggcaaggaga gagggtggag gctggcactt ggggagggac ttggggaggt gagtggtggg    3360
gacaggcagg ccctgggtct tccctggagg cagctgggc ctgagactgg tccaggtgaa     3420
cgcagagcac aggagggatt gagaccccgt tctgtgtcag ctgtagatgc tgaatgttgt    3480 cccctcctc ctgcgcatcc cagggctggc tggcaaggtc ctacgctccc aaaaggcttt     3540
cctgacccag ctggatgagc tgctgaccga gcacagaatg atctgggacc cagcctagcc    3600 acccgagac ctgactgagg ccttcctggc agagaaggag aaggtgagag tggctgacac     3660
ggtagggacc aggggtggtg ggttgagcgt ccggaggaa tgaggcaggc aaaaggtggg    3720
tccattggat cacttggcaa gtggcacctg ggctgacagg tgcagaatgt ggaggtcatt    3780
tgggggcttt cccgttctgt cccctgagta ccctctcagc cctgctcagg ccaaggggaa    3840
ccctgagagc agcttcaatg atgagaacct gcgcatggtg gtggctgacc tgttctttgc    3900
cgggatggtg accacctcga tcacgctggc ctggggcctc ctgctcatga tcctacgccc    3960
ggatgtgcag cgtgagccca gctggggccc agtgcagggg gcaagggagg aagggtacag   4020
gtgggggccc ctgagcttag ctgggacacc cgggactcca agcacaggct tggccaggtt   4080
cctgtaagcc taacctcctc caacacagga ggcaggagag tgtcagggct ggtcccctgg   4140
gtgctgaccc attgtgggga cgcgtgtctg tccaggccgt gtccaacaga tcgacaacgt   4200 gataggggcag gtgtggtgac cagagatggg tgaccaggct cgcatgccct gcaccactgc  4260
cgtgattcac gaggtgcagc gctttgggga catcgtcccc ctgggtgtga cccatatgac   4320
atcccgtgac atcgaagtac agggcttccg catccctaag gtaggcctgg caccctcctc   4380
accccagctc agcaccagcc cctggtgata gccccagcat ggccactgcc aggtgggccc   4440
agtctaggaa ccctggccac ccagtcctca atgccaccac atcgactgtc ccagcctggg  4500 tgtgggggtgc agagtatagg cagggctggc ctgtccatcc agagcccccag tctagtgggg  4560 aaggcagacc aggacctgcc agaatgttgg aggacccccaa tacctgtagg gagagggta    4620 gcgtgggcgc tccaggagg tgtgactgcg ccctgccgtg gggtcggaga gggtgctctg    4680
gagcttctcg ggcacaggac tagttgacag agtccagctg tgtgccaggc agtgtgtgtc   4740
ccctgtgtgc ttgggggtcc cagcatccta gagtccagtc cccactctca ccctgcatct   4800
cctgcccagg ggatgatgct cttcaccaac ctgtcatcgg tgctgaagga tgaggccgtc  4860
tggaagaagc ccttccgctt ccaccccgaa cacttcctgg atgcccaggg ccactttgtg   4920
aagccggagg ccttcctgcc tttctcagca gtgcctgtg gggagcccgg ctcctgtccc   4980
cttccgtgga gtcttgcagg ggtatcaccc gggagccagg ctcactgacg ccctccctc   5040 cccacaggcc gccgtgcatg cctcgggcca gcccctggcc cgcatagagc tcttcctctt  5100
```

```
cttcacctcc ctgctgcagc acttcagctt ctcggtgccc accggacagc cccggcccag      5160
ccactctcgt gtcgtcggct ttctggtgac gccatccccc tatgagcttt gtgctgtgcc      5220
ccgctagagt tgctcctcag ctgggaccct gttgtacaat aaattagtct agtggctccc      5280
acttggtttc tgtatccagt ctgggcccct gccaaggtcc tggtt                      5325
```

<210> SEQ ID NO 9
<211> LENGTH: 21
<212> TYPE: DNA
<213> ORGANISM: Artificial
<220> FEATURE:
<223> OTHER INFORMATION: synthetic primer

<400> SEQUENCE: 9
agcagagggc aaaggccatc a                                                21

<210> SEQ ID NO 10
<211> LENGTH: 21
<212> TYPE: DNA
<213> ORGANISM: Artificial
<220> FEATURE:
<223> OTHER INFORMATION: synthetic primer

<400> SEQUENCE: 10
ctctctgccc agctcggact a                                                21

<210> SEQ ID NO 11
<211> LENGTH: 21
<212> TYPE: DNA
<213> ORGANISM: Artificial
<220> FEATURE:
<223> OTHER INFORMATION: synthetic primer

<400> SEQUENCE: 11
ctttataagg gaagggtcac g                                                21

<210> SEQ ID NO 12
<211> LENGTH: 21
<212> TYPE: DNA
<213> ORGANISM: Artificial
<220> FEATURE:
<223> OTHER INFORMATION: synthetic primer

<400> SEQUENCE: 12
aggggagcct cagcacctct g                                                21

<210> SEQ ID NO 13
<211> LENGTH: 21
<212> TYPE: DNA
<213> ORGANISM: Artificial
<220> FEATURE:
<223> OTHER INFORMATION: synthetic primer

<400> SEQUENCE: 13
ggtgatcctg gcttgacaag a                                                21

<210> SEQ ID NO 14
<211> LENGTH: 21
<212> TYPE: DNA
<213> ORGANISM: Artificial
<220> FEATURE:
<223> OTHER INFORMATION: synthetic primer

<400> SEQUENCE: 14
ccacggaaat ctgtctctgt c                                                21

<210> SEQ ID NO 15
<211> LENGTH: 21
<212> TYPE: DNA
<213> ORGANISM: Artificial
<220> FEATURE:
<223> OTHER INFORMATION: synthetic primer

<400> SEQUENCE: 15
tggtggggct aatgccttca t    21

<210> SEQ ID NO 16
<211> LENGTH: 21
<212> TYPE: DNA
<213> ORGANISM: Artificial
<220> FEATURE:
<223> OTHER INFORMATION: synthetic primer

<400> SEQUENCE: 16
ccggcccctg acactccttc t    21

<210> SEQ ID NO 17
<211> LENGTH: 21
<212> TYPE: DNA
<213> ORGANISM: Artificial
<220> FEATURE:
<223> OTHER INFORMATION: synthetic primer

<400> SEQUENCE: 17
ggtggatggt ggggctaatg c    21

<210> SEQ ID NO 18
<211> LENGTH: 21
<212> TYPE: DNA
<213> ORGANISM: Artificial
<220> FEATURE:
<223> OTHER INFORMATION: synthetic primer

<400> SEQUENCE: 18
cttcccagtt cccgctttgt g    21

<210> SEQ ID NO 19
<211> LENGTH: 21
<212> TYPE: DNA
<213> ORGANISM: Artificial
<220> FEATURE:
<223> OTHER INFORMATION: synthetic primer

<400> SEQUENCE: 19
acggggaagg cgacccctta c    21

<210> SEQ ID NO 20
<211> LENGTH: 21
<212> TYPE: DNA
<213> ORGANISM: Artificial
<220> FEATURE:
<223> OTHER INFORMATION: synthetic primer

<400> SEQUENCE: 20
gagctcgccc tgcagagact c    21

<210> SEQ ID NO 21
<211> LENGTH: 21
<212> TYPE: DNA
<213> ORGANISM: Artificial
<220> FEATURE:

<223> OTHER INFORMATION: synthetic primer

<400> SEQUENCE: 21
agagcacagg agggattgag a                                              21

<210> SEQ ID NO 22
<211> LENGTH: 21
<212> TYPE: DNA
<213> ORGANISM: Artificial
<220> FEATURE:
<223> OTHER INFORMATION: synthetic primer

<400> SEQUENCE: 22
attcctcctg ggacgctcaa c                                              21

<210> SEQ ID NO 23
<211> LENGTH: 21
<212> TYPE: DNA
<213> ORGANISM: Artificial
<220> FEATURE:
<223> OTHER INFORMATION: synthetic primer

<400> SEQUENCE: 23
ccgttctgtc ccgagtatgc t                                              21

<210> SEQ ID NO 24
<211> LENGTH: 21
<212> TYPE: DNA
<213> ORGANISM: Artificial
<220> FEATURE:
<223> OTHER INFORMATION: synthetic primer

<400> SEQUENCE: 24
cccctgcact gtttcccaga t                                              21

<210> SEQ ID NO 25
<211> LENGTH: 21
<212> TYPE: DNA
<213> ORGANISM: Artificial
<220> FEATURE:
<223> OTHER INFORMATION: synthetic primer

<400> SEQUENCE: 25
ggaggcaaga aggagtgtca g                                              21

<210> SEQ ID NO 26
<211> LENGTH: 21
<212> TYPE: DNA
<213> ORGANISM: Artificial
<220> FEATURE:
<223> OTHER INFORMATION: synthetic primer

<400> SEQUENCE: 26
accaatctgg gcagtcagag t                                              21

<210> SEQ ID NO 27
<211> LENGTH: 21
<212> TYPE: DNA
<213> ORGANISM: Artificial
<220> FEATURE:
<223> OTHER INFORMATION: synthetic primer

<400> SEQUENCE: 27
ggccggaccc cctgggtgct g                                              21

```
<210> SEQ ID NO 28
<211> LENGTH: 21
<212> TYPE: DNA
<213> ORGANISM: Artificial
<220> FEATURE:
<223> OTHER INFORMATION: synthetic primer

<400> SEQUENCE: 28
gctggtgctg agctggggtg a                                              21

<210> SEQ ID NO 29
<211> LENGTH: 21
<212> TYPE: DNA
<213> ORGANISM: Artificial
<220> FEATURE:
<223> OTHER INFORMATION: synthetic primer

<400> SEQUENCE: 29
tagagtccag tccccactct c                                              21

<210> SEQ ID NO 30
<211> LENGTH: 21
<212> TYPE: DNA
<213> ORGANISM: Artificial
<220> FEATURE:
<223> OTHER INFORMATION: synthetic primer

<400> SEQUENCE: 30
agactccacg gaaggggaca g                                              21

<210> SEQ ID NO 31
<211> LENGTH: 21
<212> TYPE: DNA
<213> ORGANISM: Artificial
<220> FEATURE:
<223> OTHER INFORMATION: synthetic primer

<400> SEQUENCE: 31
tcacccagga gccaggctca c                                              21

<210> SEQ ID NO 32
<211> LENGTH: 21
<212> TYPE: DNA
<213> ORGANISM: Artificial
<220> FEATURE:
<223> OTHER INFORMATION: synthetic primer

<400> SEQUENCE: 32
tgatcccaac gagggcgtga g                                              21
```